(12) United States Patent
McKenna

(10) Patent No.: US 11,116,667 B1
(45) Date of Patent: Sep. 14, 2021

(54) PROTECTIVE EYE PIECES HAVING ROTATABLE ADJUSTER

(71) Applicant: Louis H. McKenna, Roseville, MN (US)

(72) Inventor: Louis H. McKenna, Roseville, MN (US)

( * ) Notice: Subject to any disclaimer, the term of this patent is extended or adjusted under 35 U.S.C. 154(b) by 0 days.

(21) Appl. No.: 17/157,482

(22) Filed: Jan. 25, 2021

Related U.S. Application Data

(60) Provisional application No. 63/130,633, filed on Dec. 25, 2020.

(51) Int. Cl.
*A61F 9/02* (2006.01)
*A63B 33/00* (2006.01)

(52) U.S. Cl.
CPC ............ *A61F 9/027* (2013.01); *A61F 9/026* (2013.01); *A63B 33/004* (2020.08)

(58) Field of Classification Search
CPC . A61F 9/026; A61F 9/027; G02C 7/02; A63B 33/002; A63B 33/004
USPC .......................................................... 2/448
See application file for complete search history.

(56) References Cited

U.S. PATENT DOCUMENTS

| | | | |
|---|---|---|---|
| 4,607,398 A * | 8/1986 | Faulconer | A44B 11/14 2/452 |
| 5,357,654 A | 10/1994 | Hsing-Chi | |
| 5,410,763 A | 5/1995 | Bolle | |
| 5,611,644 A | 3/1997 | Lutz | |
| 5,845,341 A | 12/1998 | Barthold et al. | |
| 5,857,221 A | 1/1999 | Geneve et al. | |
| 7,181,780 B1 | 2/2007 | Chiang | |
| 8,434,200 B2 | 5/2013 | Chen | |
| 8,850,627 B2 * | 10/2014 | Chiang | A63B 33/002 2/448 |
| 9,743,701 B2 | 8/2017 | Javorek et al. | |
| 10,156,347 B2 | 12/2018 | Pontano et al. | |
| 10,357,401 B2 * | 7/2019 | Hsu | A42B 3/085 |
| 10,492,568 B2 | 12/2019 | Burns et al. | |
| 2016/0271482 A1 | 9/2016 | Garland et al. | |
| 2018/0250556 A1 * | 9/2018 | Souweine Capella | A42B 3/145 |

FOREIGN PATENT DOCUMENTS

| | | |
|---|---|---|
| CN | 204065566 U | 12/2014 |
| CN | 105310823 B | 5/2018 |
| CN | 111329653 A | 6/2020 |
| GB | 2464749 A | 5/2010 |
| JP | 2014155591 A | 8/2014 |

(Continued)

OTHER PUBLICATIONS

"Seasoft Sea-Dial™ Mask Strap," Seasoft, seasoftscuba.com, accessed Oct. 20, 2020, (one page).

(Continued)

*Primary Examiner* — Katherine M Moran

(57) ABSTRACT

The present pair of eye pieces may have a rotatable adjuster on the super structure of the eye pieces or on the headband between the eye pieces. When the rotatable adjuster is rotated one way, the headband decreases in effective length and tightens about the head of a user. When the rotatable adjuster is rotated the other way, the headband increases in effective length and loosens about the head of the user. With a rotatable adjuster, increases and decreases in length may be made in minute increments.

16 Claims, 10 Drawing Sheets

(56) References Cited

FOREIGN PATENT DOCUMENTS

| KR | 20150125270 A | 11/2015 |
|----|---------------|---------|
| WO | 2010051603 A1 | 5/2010  |
| WO | 2016044350 A1 | 3/2016  |

OTHER PUBLICATIONS

"Flexible Bicycle Helmet Dial-Fit Closure System," Aurora Sports, helmetsupplier.com, Mar. 16, 2019, (seven pages).
"Dye I5 GSR Pro Mask / Goggle Strap—Black / Grey—Paintball," Dye, amazon.com, ASIN: B07F2PSSVF, accessed Oct. 20, 2020, (five pages).

* cited by examiner

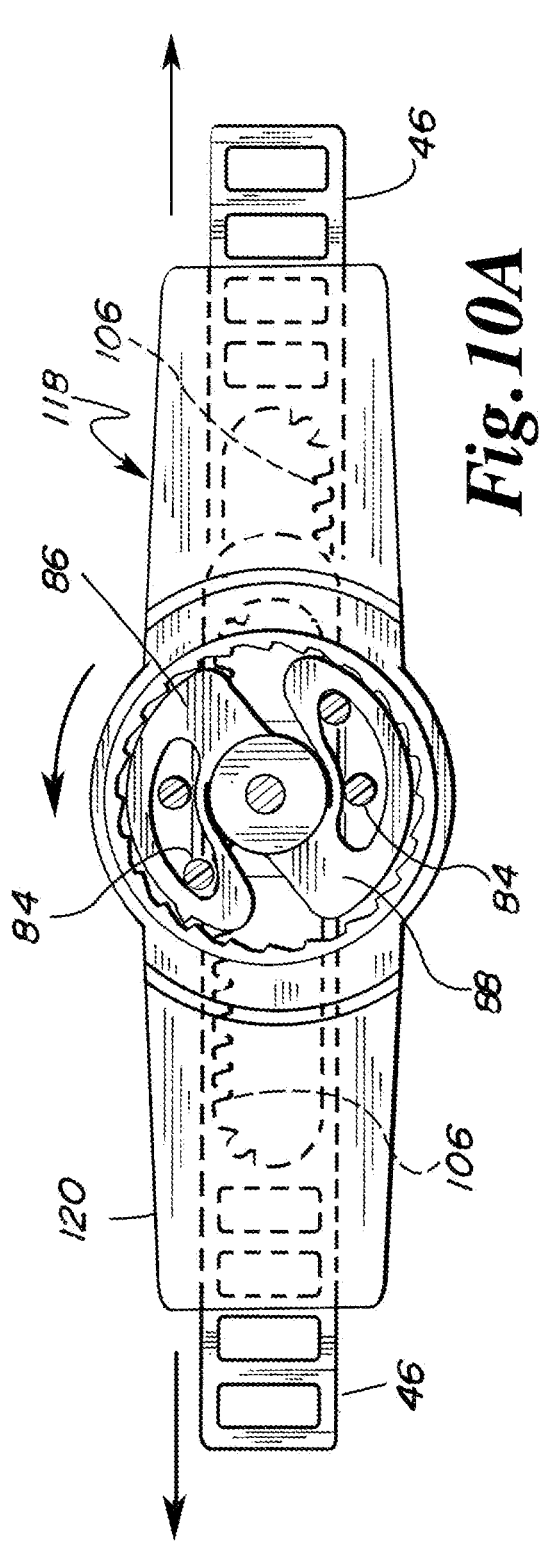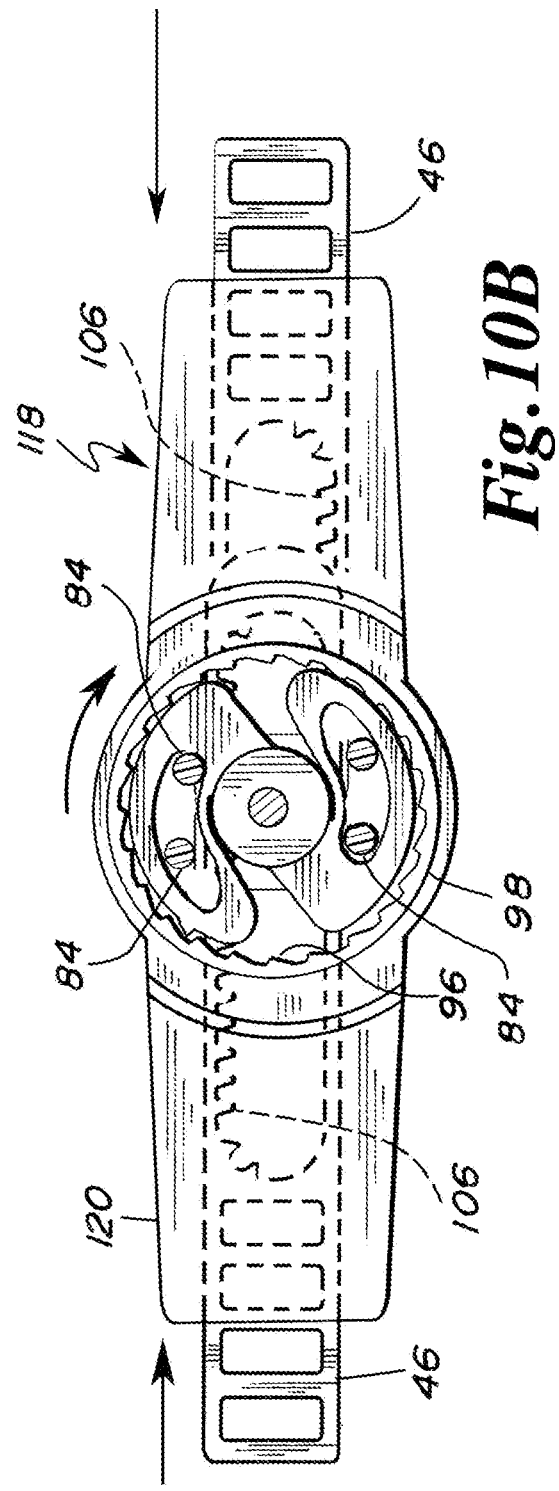

PROTECTIVE EYE PIECES HAVING ROTATABLE ADJUSTER

This application claims the benefit under 35 U.S.C. 119(e) of the U.S. provisional patent application No. 63/130,633 filed Dec. 25, 2020, which provisional patent application is hereby incorporated by reference in its entirety into this application.

FIELD OF THE INVENTION

The present invention relates to eye pieces, particularly to protective eye pieces, and specifically to protective eye pieces covering the right eye and left eye independently of each other.

BACKGROUND OF THE INVENTION

Comfort and doing the job may be two different things. In an extreme example, Yosemite climbers have special climbing shoes that do the job, i.e., hold on a ledge extending a millimeter or less from the rock face. The Yosemite climbers sacrifice comfort for this function. We see in the climbing documentaries that they rub their feet after their successful climbs.

Swimming goggles can be difficult to 1) fit comfortably and 2) do the job, i.e., keep water out of the eyes. Unknown to the swimless, the difference between 1) fitting comfortably and 2) doing the job, often requires a very minute adjustment in the tightness of the headband around the back of the swimmer's head.

Recently, with the Covid 19 pandemic, employing some type of eye wear has become popular to guard against the virus entering the eyes. Here especially it is important that each of the factors of comfort and doing the job is maximized.

SUMMARY OF THE INVENTION

A feature of the present invention is the provision in a pair of eye pieces that covers each of the right eye and left eye individually of the other, of a right eye superstructure, where the right eye superstructure includes a right eye piece, where the right eye piece is transparent to permit the right eye to see through the right eye piece, and where the right eye piece includes a right eye piece circumference extending 360 degrees about the right eye piece.

Another feature of the present invention is the provision in a pair of eye pieces that covers each of the right eye and left eye individually of the other, of a left eye superstructure, where the left eye superstructure includes a left eye piece, where the left eye piece is transparent to permit the left eye to see through the left eye piece, and where the left eye piece includes a left eye piece circumference extending 360 degrees about the left eye piece.

Another feature of the present invention is the provision in a pair of eye pieces that covers each of the right eye and left eye individually of the other, of a right eye resilient seal extending rearwardly from the right eye piece circumference such that the right eye resilient seal extends 360 degrees about the right eye piece, and where the right eye resilient seal extends 360 degrees about the right eye of a user.

Another feature of the present invention is the provision in a pair of eye pieces that covers each of the right eye and left eye individually of the other, of a left eye resilient seal extending rearwardly from the left eye piece circumference such that the left eye resilient seal extends 360 degrees about the left eye piece, and where the left eye resilient seal extends 360 degrees about the left eye of the user.

Another feature of the present invention is the provision in a pair of eye pieces that covers each of the right eye and left eye individually of the other, of the right eye piece being spaced from the left eye piece.

Another feature of the present invention is the provision in a pair of eye pieces that covers each of the right eye and left eye individually of the other, of the right eye resilient seal being spaced from the left eye resilient seal.

Another feature of the present invention is the provision in a pair of eye pieces that covers each of the right eye and left eye individually of the other, of a resilient bridge extending between the right eye superstructure and the left eye superstructure.

Another feature of the present invention is the provision in a pair of eye pieces that covers each of the right eye and left eye individually of the other, of a resilient headband engaged between the right and left superstructures, where the resilient head band extends about a head of the user.

Another feature of the present invention is the provision in a pair of eye pieces that covers each of the right eye and left eye individually of the other, of a first rotatable adjustment apparatus engaged to the resilient headband and increasing and decreasing an effective length of the headband to tighten and loosen the right and left eye resilient seals about the right and left eyes of the user.

Another feature of the present invention is the provision in a pair of eye pieces that covers each of the right eye and left eye individually of the other, of the first rotatable adjustment apparatus being engaged to the right eye superstructure.

Another feature of the present invention is the provision in a pair of eye pieces that covers each of the right eye and left eye individually of the other, of the first rotatable adjustment apparatus being engaged to the left eye superstructure.

Another feature of the present invention is the provision in a pair of eye pieces that covers each of the right eye and left eye individually of the other, of a second rotatable adjustment apparatus being engaged to the left eye superstructure.

Another feature of the present invention is the provision in a pair of eye pieces that covers each of the right eye and left eye individually of the other, of the first rotatable adjustment apparatus being intermediate of the right and left eye superstructure and engaged to the resilient headband such that a first portion of the resilient headband extends from the first rotatable adjustment apparatus to the right eye superstructure and such that a second portion of the resilient headband extends from the first rotatable adjustment apparatus to the left eye superstructure.

Another feature of the present invention is the provision in a pair of eye pieces that covers each of the right eye and left eye individually of the other, of the first rotatable adjustment apparatus including a base and a rack and pinion apparatus, where the rack and pinion apparatus includes a pinion driving a rack in first and second directions, where the rack is engaged to the resilient headband, where the rack when driven by the pinion in the first direction increases an effective length of the headband, where the rack when driven by the pinion in the second direction decreases the effective length of the headband, and where the rack slides in the first and second directions in a slot formed in the base.

Another feature of the present invention is the provision in a pair of eye pieces that covers each of the right eye and left eye individually of the other, of the base of the first rotatable adjustment apparatus being integral with one of the right and left eye superstructures.

Another feature of the present invention is the provision in a pair of eye pieces that covers each of the right eye and left eye individually of the other, of the first rotatable adjustment apparatus including a base and a ratchet apparatus, where the base includes an annulus with a toothed inner face, where the ratchet apparatus includes gearing having a pawl, where the pawl engages the toothed inner face of the annulus, where the gearing engages the resilient headband, and where the pawl at all times permits the effective distance of the headband to be decreased.

Another feature of the present invention is the provision in a pair of eye pieces that covers each of the right eye and left eye individually of the other, of the rotatable adjustment apparatus including a base having a toothed gear, a rack and pinion apparatus having a rack and pinion, and a pawl apparatus having a pawl that engages the toothed gear, where the pawl is resiliently engaged between the toothed gear and the pinion, where the pinion is lockable by an engagement between the pawl and toothed gear such that the rack may be slid in only one of the first and second directions, and where the pinion is unlockable by a disengagement between the pawl and toothed gear such that the rack may be slid in each of the first and second directions.

Another feature of the present invention is the provision in a pair of eye pieces that covers each of the right eye and left eye individually of the other, of the first rotatable adjustment apparatus being engaged to the right eye superstructure and being turnable clockwise and counter-clockwise, where the effective length of the headband is decreased when the first rotatable adjustment apparatus is turned clockwise, and where the effective length of the headband being increased when the first rotatable adjustment apparatus is turned counter-clockwise.

Another feature of the present invention is the provision in a pair of eye pieces that covers each of the right eye and left eye individually of the other, of first rotatable adjustment apparatus being engaged to the right eye superstructure and being turnable clockwise and counter-clockwise, the effective length of the headband being increased when the first rotatable adjustment apparatus is turned clockwise, the effective length of the headband being decreased when the first rotatable adjustment apparatus is turned counter-clockwise.

Another feature of the present invention is the provision in a pair of eye pieces that covers each of the right eye and left eye individually of the other, of a second rotatable adjustment apparatus being engaged to the left eye superstructure and being turnable clockwise and counter-clockwise, where the effective length of the headband is decreased when the second rotatable adjustment apparatus is turned clockwise, and where the effective length of the headband is increased when the second rotatable adjustment apparatus is turned counter-clockwise.

Another feature of the present invention is the provision in a pair of eye pieces that covers each of the right eye and left eye individually of the other, of a second rotatable adjustment apparatus engaged to the left eye superstructure and being turnable clockwise and counter-clockwise, where the effective length of the headband is increased when the first rotatable adjustment apparatus is turned clockwise, and where the effective length of the headband is decreased when the first rotatable adjustment apparatus is turned counter-clockwise.

An advantage of the present invention is that very small changes may be made in the effective length of a headband for a pair of eye pieces. Since very small changes in the length may be made, both of comfort and a highly effective seal may be realized.

Another advantage of the present invention is that the rotatable adjustment apparatus is at an accessible location. This accessible location is at the right corner of the right eye or at the left corner of the left eye, where the rotatable adjustment apparatus is engaged to the superstructure of the right eye piece or the superstructure of the left eye piece. A user may simply raise his or her right or left hand up to such locations, instead of reaching back behind his or her head to rotate a mechanism in the back of his or her head.

Another advantage of the present invention is that the rotatable adjustment apparatus includes a base. This base is the superstructure of the right eye piece or the superstructure of the left eye piece. The base is secure for at least two reasons. First, the superstructure is formed of a rigid or semi-rigid plastic. Second, the superstructure is secured on the face about the eye by a resilient seal extending for 360 degrees about the eye. Third, the companion superstructure is also secured on the face about the other eye by a resilient seal extending for 360 degrees about the other eye. Fourth, the headband holds the superstructure and resilient seals in place.

Another advantage is that water is kept out of the eyes of the user.

Another advantage is that particles as small as 50 to 150 nanometers in diameter may be kept out of the eyes. This includes particles the size of the Covid 19 virus.

Another advantage is that the rotatable adjustment apparatus may be used for macroscopic adjustment and microscopic adjustment. In other words, the rotatable adjustment apparatus may be used for both relatively great and relatively small increases and decreases in the length of the headband.

Another advantage is that buckles may be outright eliminated from a headband of the present invention.

Another advantage is that a headband may have a single length adjustor, with such single length adjustor being the rotatable adjustment apparatus engaged to either the right eye superstructure or the left eye superstructure.

Another advantage is that the step of increasing or decreasing the length of the headband via the rotatable adjustment apparatus is a one handed operation.

Another advantage is that the step of increasing or decreasing the length of the headband via the rotatable adjustment apparatus is a thumb and forefinger operation, with the thumb and forefinger that are used being on one hand.

BRIEF DESCRIPTION OF THE DRAWINGS

FIG. 10A is a view at lines 10A-10A of FIG. 9A with the rotatable adjustment apparatus being turned counter-clockwise to increase the effective length of the headband.

FIG. 10B is a view of FIG. 10A with the rotatable adjustment apparatus being turned clockwise to decrease the effective length of the headband.

DESCRIPTION

Figure 1A:
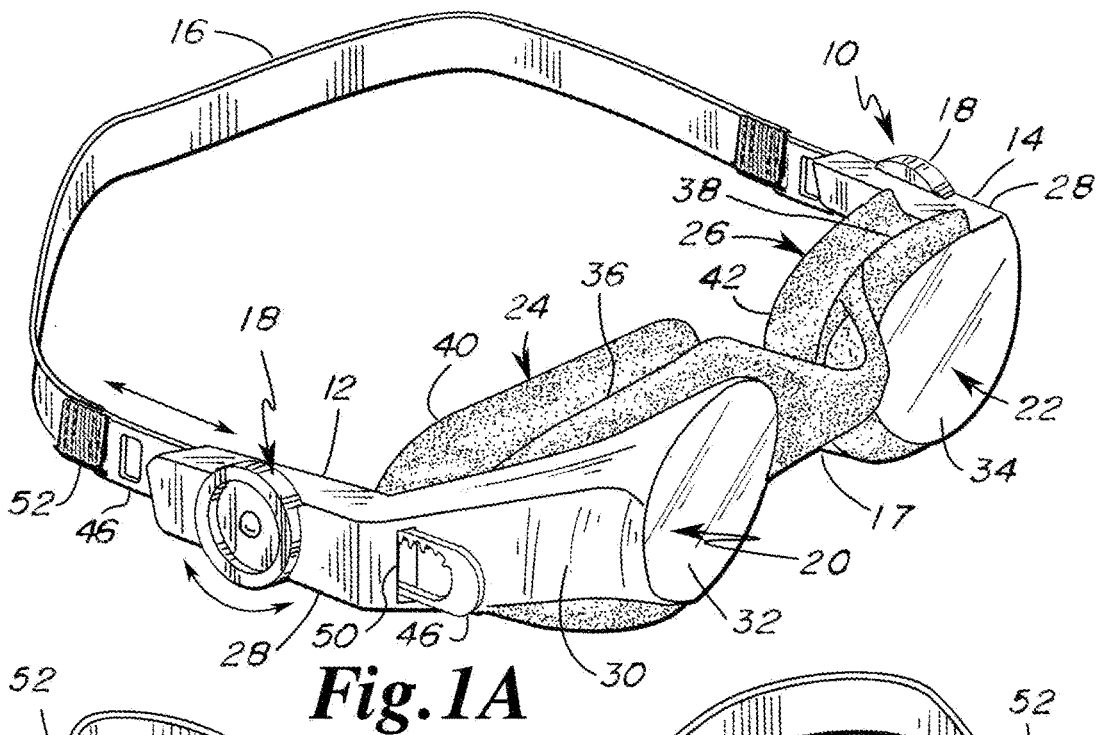
FIG. 1A shows a three-quarters perspective view of a first embodiment of the present invention where a pair of eye pieces have a rotatable adjustment apparatus adjacent to each of the eye pieces and a continuous headband.

As shown in FIG. 1A, a first embodiment of the present eye piece pair is designated by the reference number 10. Eye piece pair 10 includes a right eye superstructure 12, a left eye superstructure 14, a resilient and flexible headband 16 engaging each of the superstructures 12, 14, a resilient and flexible bridge 17 engaging each of the superstructures 12, 14, a right rotatable adjustment apparatus 18, and a left rotatable adjustment apparatus 18. The right eye superstructure 12 includes a right eye piece 20 and the left eye superstructure 14 includes a left eye piece 22. Extending rearwardly from the right eye piece 20 is a resilient right seal 24. Extending rearwardly from the left eye piece 22 is a resilient left seal 26.

Each of the superstructures 12, 14 is preferably integral and one-piece and formed of a hard or semi-rigid plastic or polymer material. Each of the superstructures 12, 14 includes a temple portion 28 extending generally toward the ear. The temple portion 28 includes an outer side, an inner side, a top side, and a bottom side. The temple portion 28 further has a rear end adjacent to the ear and a front portion. Temple portion 28 is tubular.

Each of the superstructures 12, 14 further includes an oblique portion 30. The oblique portion 30 is integrally engaged to the front end of the temple portion 28 and extends therefrom to the eye piece 20 or 22. The oblique portion 30 includes an outer side, an inner side, a top side, and a bottom side. The oblique portion 30 further includes a rear end integrally engaged to the front end of the temple portion 28 and a front end integrally engaged to the eye piece 20 or 22. Oblique portion 30 is tubular.

Each of the superstructures 12, 14 further includes one eye piece 20, 22, respectively. Each of the eye pieces 20, 22 includes an outer end portion that is integrally engaged with the oblique portion 30. Each of the eye pieces 20, 22 includes an inner end portion. The inner end portions of the eye pieces 20, 22 are spaced from each other. Resilient and flexible bridge 17 extends from the inner end portion of eye piece 20 to the inner end portion of eye piece 22. Each of the eye pieces 20, 22 includes a respective front flat see through plate 32, 34. Each of the plates 32, 34 includes a curved perimeter. Each of the plates 32, 34 may be disposed in a plane set at a right angle to an axis of its respective temple portion 28. Eye piece 20 includes an endless sidewall 33 extending rearwardly from see through plate 32. Eye piece 22 includes an endless sidewall 35 extending rearwardly from see through plate 34.

Each of the resilient seals 24, 26 includes a respective base portion 36, 38. Base portions 36, 38 are engaged to and extend rearwardly from its respective endless sidewall 33, 35 of its respective eye pieces 20, 22. Each of the base portions 36, 38 may further be engaged to the inner face of its respective oblique portion 28. Each of the resilient seals 24, 26 includes a respective flared or undulating portion 40, 42 that sealingly engages the face about the eyes. Each of the base portions 36, 38 and each of the flared or undulating portion 40, 42 extend for 360 degrees about its respective eye such that each of the resilient seals 24, 26 extend for 360 degrees about its respective eye.

Seal 24 and eye piece 20 form a first suction cup. That is when seal 24 is pressed against the face about the right eye air is pushed out of the space between the seal 24 and eye piece 20 such that when the seal 24 is lifted off the space a popping sound is heard, which popping sound is the result of air being drawn back into the first suction cup.

Seal 26 and eye piece 22 form a second suction cup. That is when seal 26 is pressed against the face about the left eye air is pushed out of the space between the seal 26 and eye piece 22 such that when the seal 26 is lifted off the space a popping sound is heard, which popping sound is the result of air being drawn back into the second suction cup.

Figure 5A:
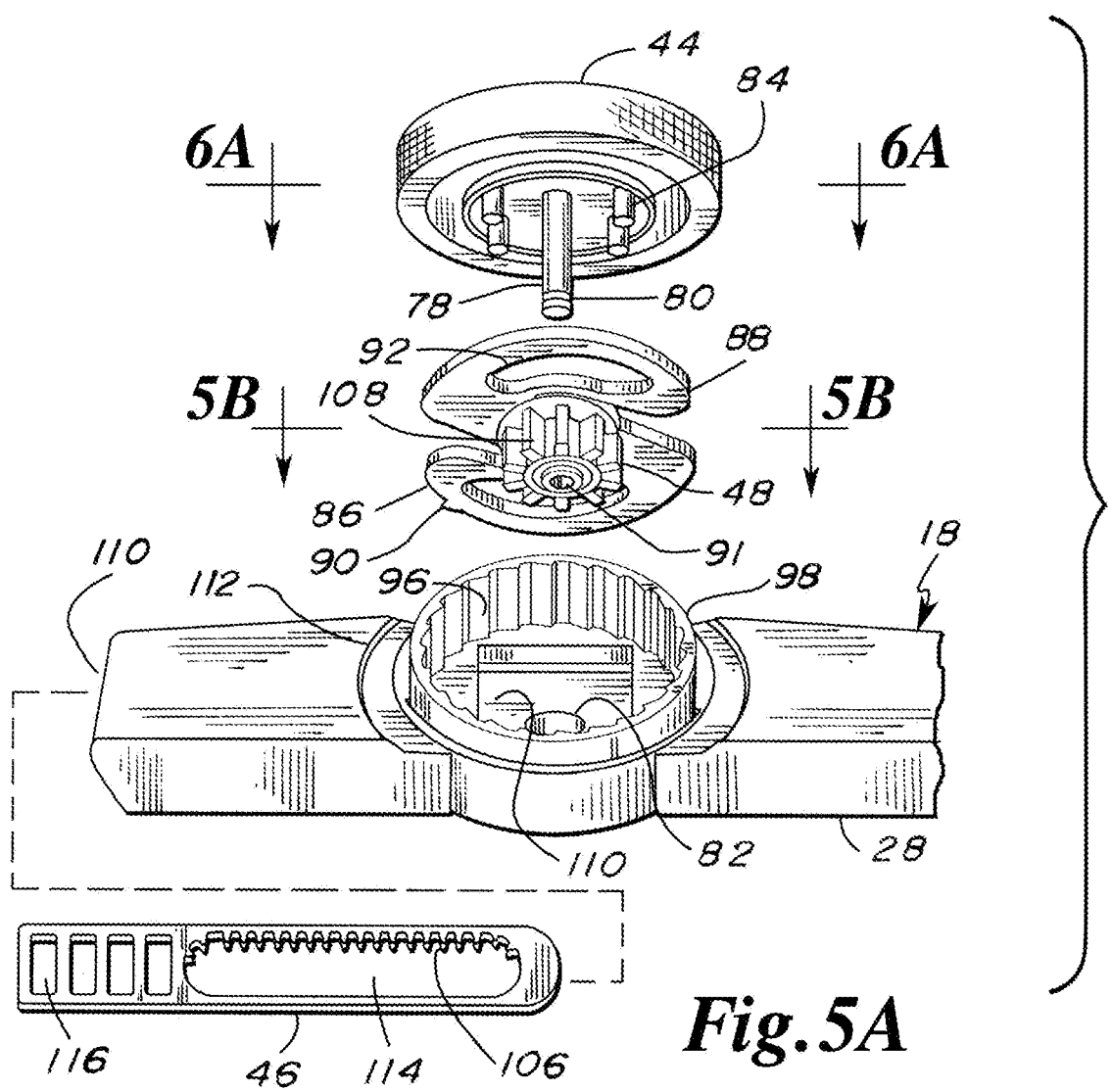
FIG. 5A is an exploded perspective view of the rotatable adjustor for any of the rotatable adjustment apparatus of FIGS. 1A-1C, 2A-2C, 3A-3C, and 4A-4C.

Temple portion 28 and oblique portion 30 are tubular. Temple portion 28 houses the rotatable adjustment apparatus 18, which apparatus 18 includes a rotatable finger disk 44, a rack 46, and a pinion 48. Pinion 48 is shown in FIG. 5A. Rotating finger disk 44 drives the rack 46 that in turn increases and decreases the length of the headband 16. Rack 46 is slideably housed in the tubular temple portion 28. A front end of the rack 46 slideably exits a slot 50 in the oblique portion 30 of the right eye superstructure 12. A rear end of the rack 46 exits a slot in the rear end of the temple portion 28. The rear end of the rack 46 is engaged, such as by an adhesive or stitching 52, to one end of the headband 16.

Figure 1B:
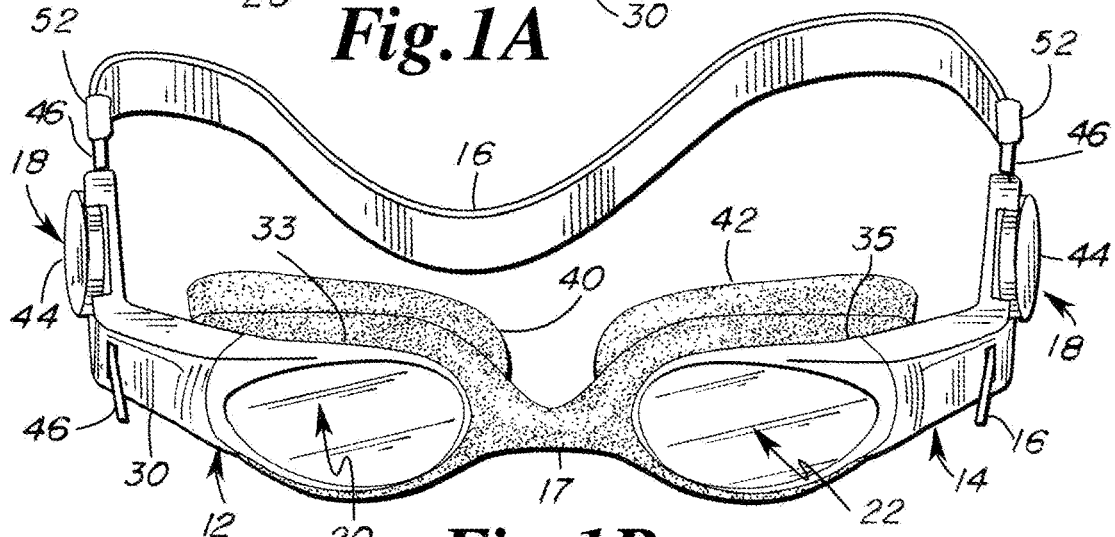
FIG. 1B shows a front perspective view of the first embodiment of FIG. 1A.

As shown in each of FIGS. 1A and 1B, the rotatable adjustment apparatus 18, including the finger disk 18 and rack 46, is engaged to each of the right eye and left eye superstructures 12, 14.

Figure 1C:
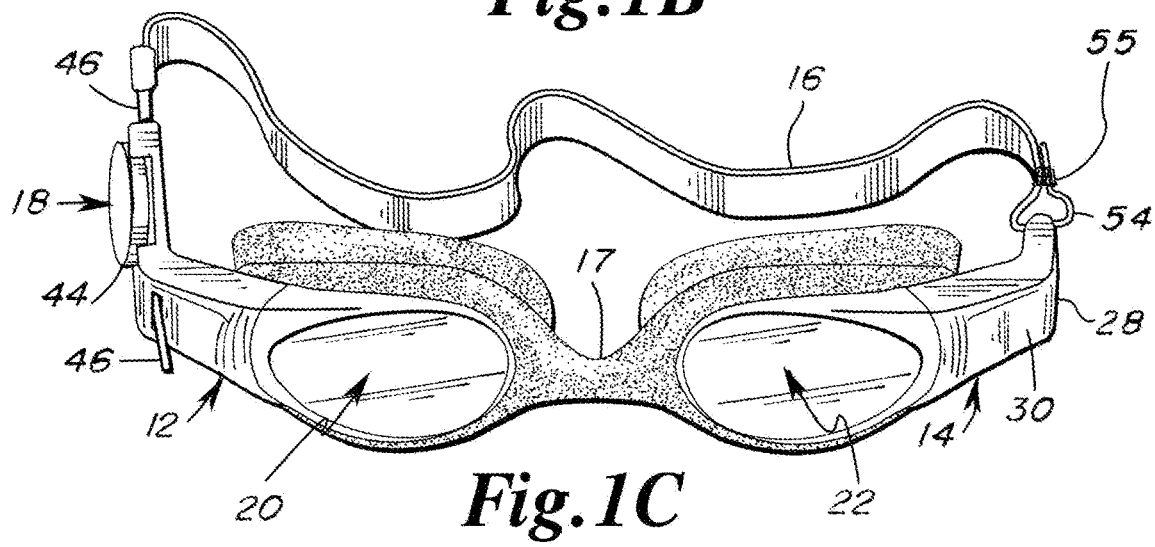
FIG. 1C shows a front perspective view of a second embodiment of the present invention where a pair of eye pieces have a single rotatable adjustment apparatus adjacent to one of the eye pieces, a non-adjustable connection adjacent to the other of the eye pieces, and a continuous headband.

As shown in FIG. 1C, the right eye superstructure 12 includes the rotatable adjustment apparatus 18, including the rack 46 and finger disk 44, while the left eye superstructure 14 does not have the rotatable adjustment apparatus 18. Instead, the left eye superstructure 14 includes a slot 76 (shown in FIG. 3C) in the rear end of the temple portion 28, which slot 76 engages a headband end portion 54, which headband end portion 54 has been inserted into the slot 76 and then secured back onto itself with adhesive or stitches 55 to form a loop, with the loop engaging such slot 76. The slot 76 opens on the outer and inner sides of the temple portion 28. This glued or stitched looped headband end portion 54 is permanent and intended to be a permanent nonadjustable connection to the left eye superstructure 14. "Permanent" means that the nonadjustable connection is disconnectable from the left eye superstructure 14 only if the integrity of the nonadjustable connection is destroyed such as by cutting or tearing or breaking of the headband end portion 54 or temple portion 28 to which the looped headband end portion 54 is connected. If desired, this permanent nonadjustable headband end portion 54 may be engaged to the rear end of the temple portion 28 of right eye superstructure 12 and the rotatable adjustment apparatus 18 may be engaged to the left eye superstructure 14. In FIG. 1C (and in FIG. 2C), the temple portion 28 having the permanent headband end portion 54 may be of a lesser length than the temple portion 28 having the rotatable adjustment apparatus 18. However, if desired, the temple portion 28 having the permanent headband end portion 54 may be of the same length as the temple portion 28 having the rotatable adjustment apparatus 18.

Headband 16 is resilient. Headband 16 is flexible. Headband 16 is stretchable. Headband 16 may be formed of an elastomer material or rubber or rubber like material. As shown in FIGS. 1A, 1B, and 1C, headband 16 includes no adjustment apparatus other than one or more ends of the headband 16 being engaged to the rotatable adjustment apparatus 18.

Figure 2A:
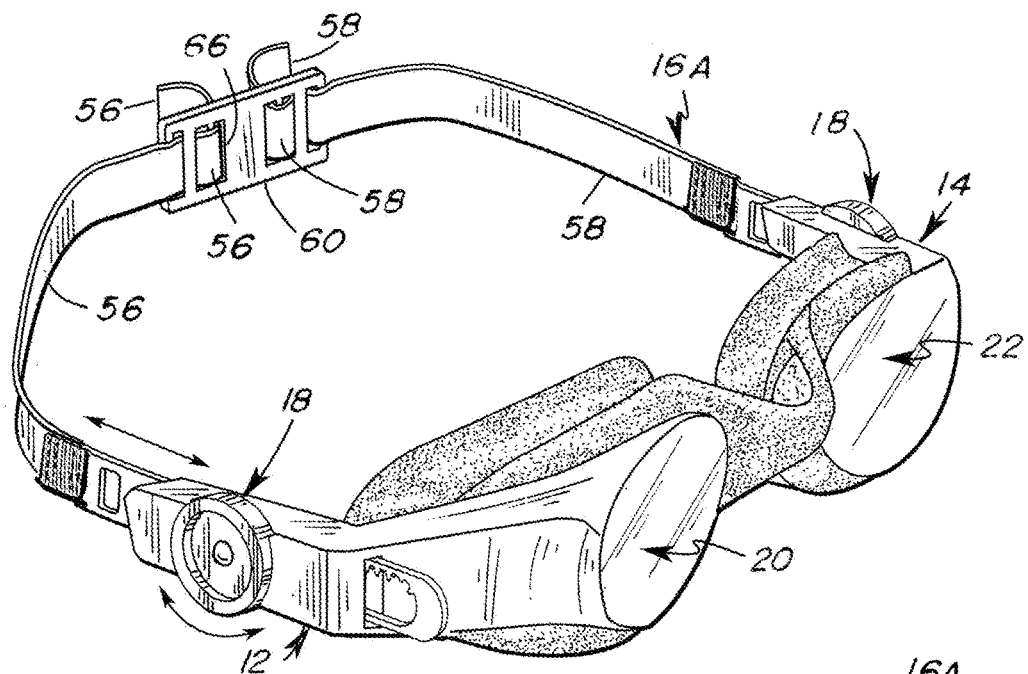
FIG. 2A shows a three-quarters perspective view of a third embodiment of the present invention where a pair of eye pieces have a rotatable adjustment apparatus adjacent to each of the eye pieces and a headband having a rear adjustment mechanism.

The embodiment of the pair of eye pieces shown in FIG. 2A is identical to the eye piece pair shown in FIG. 1A except that the headband 16A includes a first portion 56 and a second portion 58. Headband portions 56, 58 are engaged to each other by a buckle 60. Buckle 60 includes, as best shown in FIG. 2C, two opposing open T-shaped slots 62, two closed slots 64, and two closed slots 66. Resilient and flexible headband portion 56 (or 58) is fed from the outside of buckle 60 into closed slot 64 and then is fed from inside of buckle 60 into closed slot 66. Then a section of the headband portion 56 (or 58) that is adjacent to the T-shaped slot 62 is twisted such that an edge of such portion is fed into the T-shaped slot 62 and then brought into the section of the slot 62 that is parallel to slots 64, 66. Buckle 60 provides a nonrotatable means of adjustment of the length of the headband 16A.

Figure 2B:
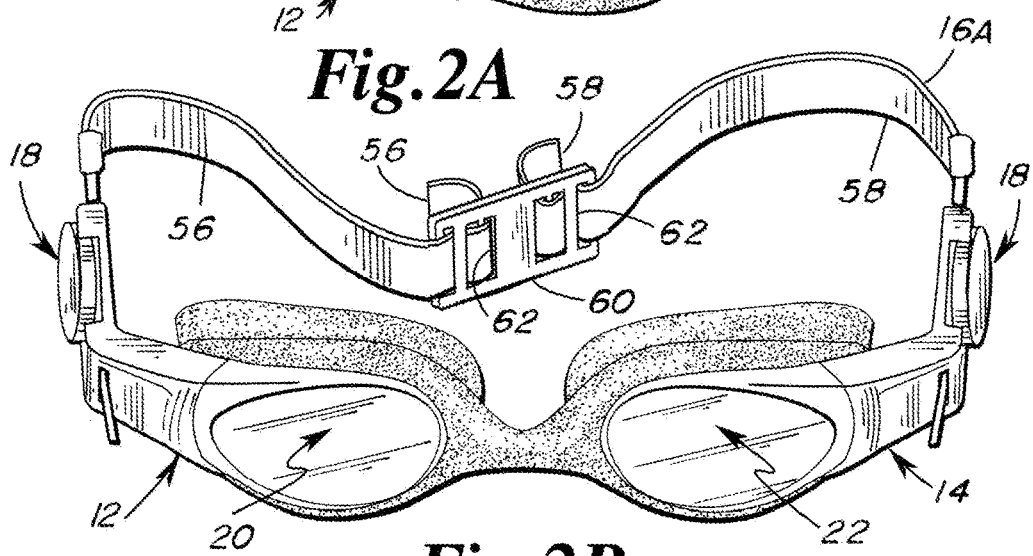
FIG. 2B shows a front perspective view of the third embodiment of FIG. 2A.
Figure 2C:
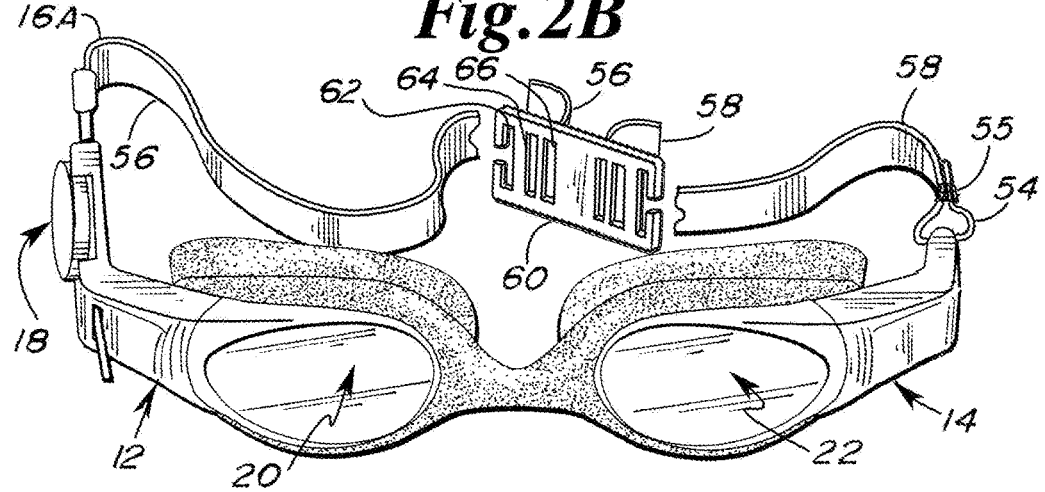
FIG. 2C shows a front perspective view of a fourth embodiment of the present invention where a pair of eye pieces have a single rotatable adjustment apparatus adjacent to one of the eye pieces, a non-adjustable connection adjacent to the other of the eye pieces, and a headband having a rear adjustment mechanism.

The embodiment of the pair of eye pieces shown in FIG. 2B is identical to the eye piece pair shown in FIGS. 1A and 1B except that the headband 16A includes the first portion 56, the second portion 58, and the buckle 60.

The embodiment of the pair of eye pieces shown in FIG. 2C is identical to the eye piece pair shown in FIG. 1C except that the headband 16A includes the first portion 56, the second portion 58, and the buckle 60. In FIG. 2C the headband portions 56, 58 are broken apart such that the structure of buckle 60 can be shown.

Figure 3A:
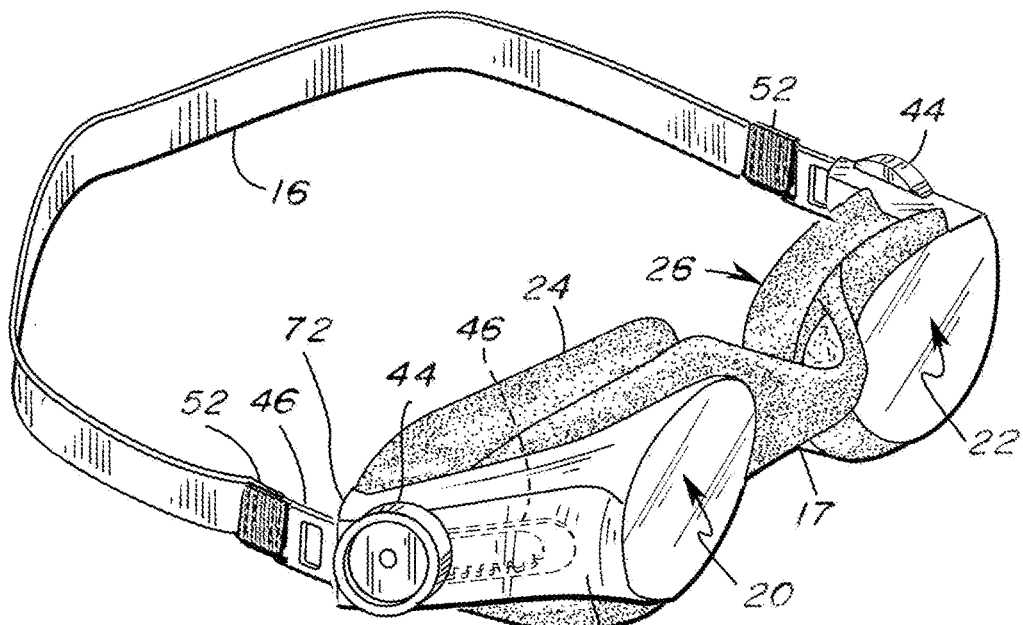
FIG. 3A shows a three-quarters perspective view of a fifth embodiment of the present invention where a pair of eye pieces have a rotatable adjustment apparatus adjacent to each of the eye pieces and a continuous headband.
Figure 3B:
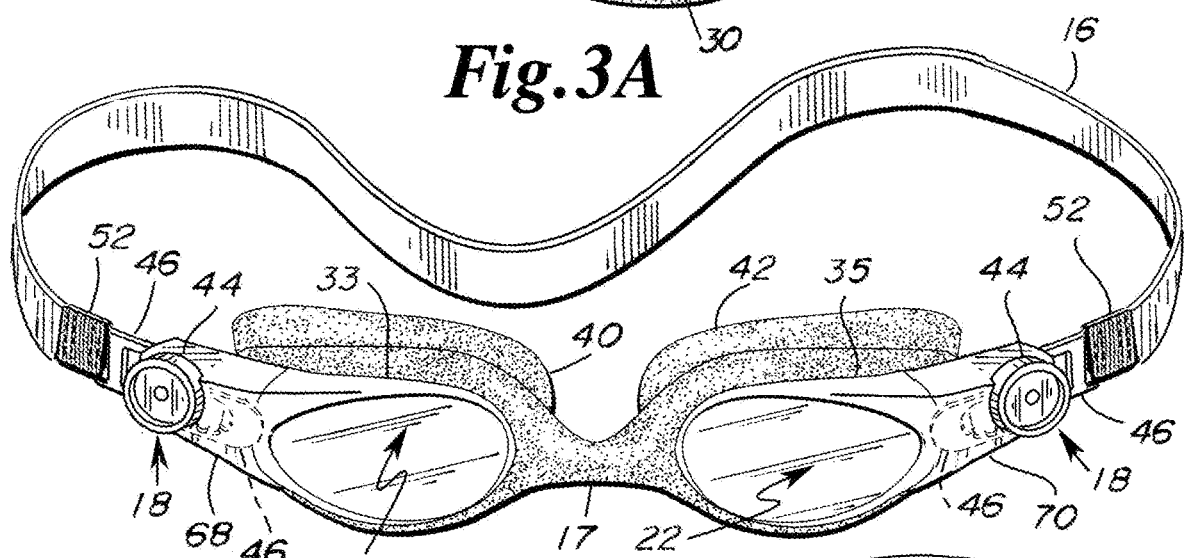
FIG. 3B shows a front perspective view of the fifth embodiment of FIG. 3A.

In FIGS. 3A and 3B, the right eye superstructure 68 and the left eye superstructure 70 are identical to the right and left eye superstructures 12, 14 except that the superstructures 68, 70 do not include the temple portion 28 and except that the inside of the superstructures 68, 70 now include features for housing rotatable adjustment apparatus 18. Oblique portion 30 is tubular to permit the distal end of the rack 46 to extend back and forth therein. The proximal end of the rack 46 slideably extends through a slot in the rear end of the oblique portion 30.

Figure 3C:
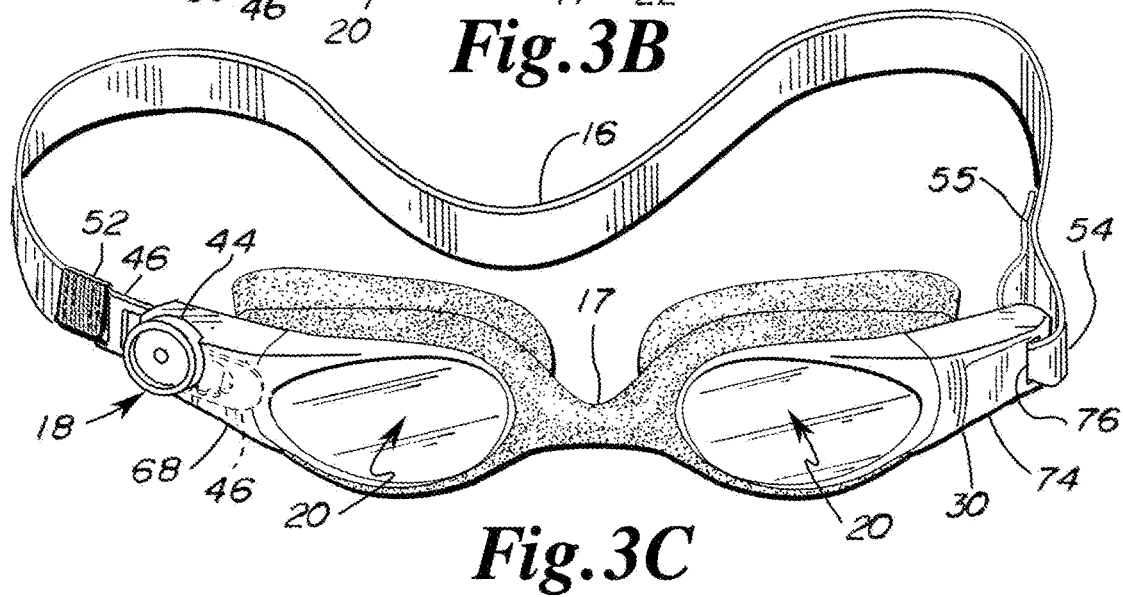
FIG. 3C shows a front perspective view of a sixth embodiment of the present invention where a pair of eye pieces have a single rotatable adjustment apparatus adjacent to one of the eye pieces, a non-adjustable connection adjacent to the other of the eye pieces, and a continuous headband.

In FIG. 3C, the right eye superstructure is the superstructure 68 shown in FIGS. 3A and 3B, while a left eye superstructure 74 is identical to the superstructure 70 of FIGS. 3A and 3B except that left eye superstructure 74 is devoid of the rotatable adjustment apparatus 18 and except that left eye superstructure 74 has a slot 76 formed in each of the front and rear sides of the oblique portion 30 so as to engage the looped headband end portion 54 that is identical to the looped headband end portion 54 shown in FIGS. 1C and 2C.

Figure 4A:
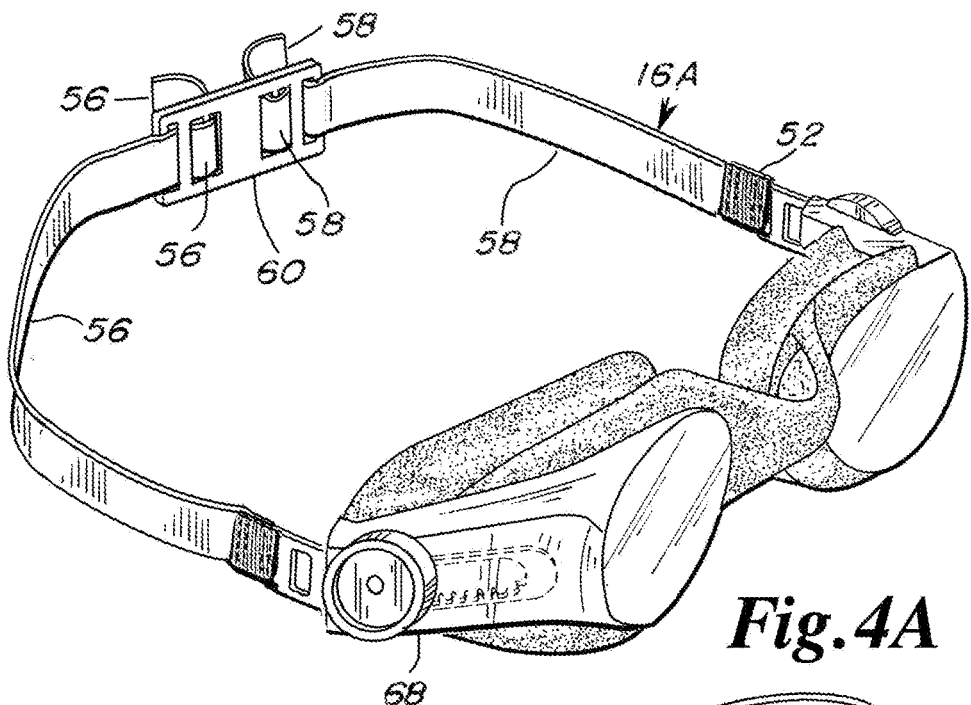
FIG. 4A shows a three-quarters perspective view of a seventh embodiment of the present invention where a pair of eye pieces have a rotatable adjustment apparatus adjacent to each of the eye pieces and a headband having a rear adjustment mechanism.

The embodiment of the pair of eye pieces shown in FIG. 4A is identical to the eye piece pair shown in FIG. 3A except that the headband 16A includes the first portion 56 and the second portion 58. Headband portions 56, 58 are engaged to each other by the buckle 60. Buckle 60 includes, as best shown in FIG. 4C, two opposing open T-shaped slots 62, two closed slots 64, and two closed slots 66. Resilient and flexible headband portion 56 (or 58) is fed from the outside of buckle 60 into closed slot 64 and then is fed from inside of buckle 60 into closed slot 66. Then a section of the headband portion 56 (or 58) that is adjacent to the T-shaped slot 62 is twisted such that an edge of such portion is fed into the T-shaped slot 62 and then brought into the section of the slot 62 that is parallel to slots 64, 66. Buckle 60 provides a nonrotatable means of adjustment of the length of the headband 16A.

Figure 4B:
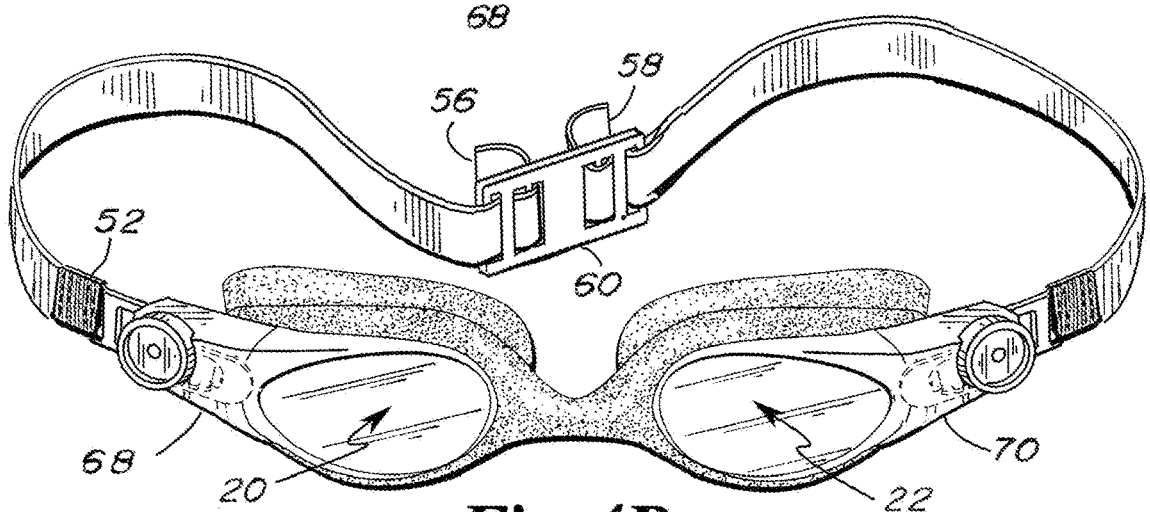
FIG. 4B shows a front perspective view of the seventh embodiment of FIG. 4A.
Figure 4C:
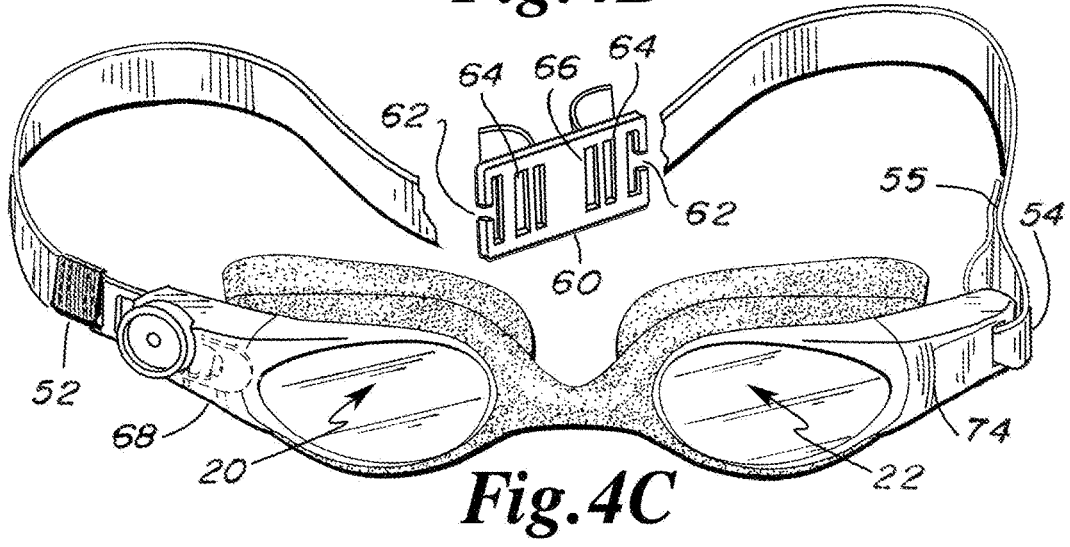
FIG. 4C shows a front perspective view of an eighth embodiment of the present invention where a pair of eye pieces have a single rotatable adjustment apparatus adjacent to one of the eye pieces, a non-adjustable connection adjacent to the other of the eye pieces, and a headband having a rear adjustment mechanism.

The embodiment of the pair of eye pieces shown in FIG. 4B is identical to the eye piece pair shown in FIGS. 3A and 3B except that the headband 16A includes the first portion 56, the second portion 58, and the buckle 60.

The embodiment of the pair of eye pieces shown in FIG. 4C is identical to the eye piece pair shown in FIG. 3C except that the headband 16A includes the first portion 56, the second portion 58, and the buckle 60. In FIG. 4C the headband portions 56, 58 are broken apart such that the structure of buckle 60 can be shown.

One embodiment of the rotatable adjustment apparatus 18 is shown in FIGS. 5A, 5B, 6A, and 6B. Rotatable adjustment apparatus 18 includes the finger driven disk 44. Disk 44 includes a central axle 78. At its distal end, axle 78 includes an annular channel 80 to which is engaged a locking washer in the form of an E or C ring after the distal end of the axle 78 has been inserted into an opening 82 in the base or temple portion 28. The locking washer lies on the inner side of temple portion 28. Disk 44 further includes four pins or shafts extending parallel to the central axle 78 and defining the corners of a rectangle, where the rectangle has adjacent uneven sides. Disk 44, axle 78, and pins 84 are one-piece and rotate as one-piece.

Rotatable adjustment apparatus 18 further includes a pinion and pawl combination 86. Combination 86 includes a pinion 48, a pawl base 88, and a pawl 90 on the pawl base 88. Disk axle 78 extends through a central through opening 91 in the combination 86, which opening 91 extends centrally through the pinion 48 and the pawl base 88. Pawl base 88 is squeezable or resilient in the radial direction. Pawl base 88 includes a pair of arcuate slots 92. End 94 of one of the slots 92 is adjacent to pawl 90. When disk 44 is turned, pins 84 drive the pinion and pawl combination 86, and the pin 84 in end 94 adjacent to pawl 90 provides enough power to pawl 90 to overcome teeth 96 of a fixed annular gear 98 molded in base or temple portion 28 of the superstructure 12 or 14. When pawl 90 is driven against the teeth 96 in either of the rotation directions, the flexible or resilient pawl base 88 flexes inwardly. This flexing is a result of the pawl base 88 being formed by two extensions 100 extending from a central region 102. Extension 100 is relatively inflexible immediately at the central region 102, but as distance from the central region 102 increases, the extension 100 becomes more flexible, especially at a thin region 104 that is spaced radially and axially from connection to the central region 102. Each of the extensions 100 has one of the arcuate slots 92.

Rotatable adjustment apparatus 18 includes the fixed gear 98 having inner endless teeth 96. Fixed gear 98 and its inner endless gear teeth 96 are integral with base or temple portion 28 of the superstructure 12 or 14. The inner tips of gear teeth 96 define a diameter that is about equal to the diameter defined by the outer edges of extension 100 of pawl base 88. Pawl 90 extends outwardly from the outer edge of one extension 100 such that pawl 90 slideably engages gear teeth 96 when pawl 90 and pawl base 88 are driven by the pins 84 of disk 44. In one rotation direction pawl 90 is retracted resiliently inwardly so as to slide over gear teeth 96 such that the barb of the pawl 90 does not catch the teeth 96, which otherwise are oriented to catch the pawl 90. In the other rotation direction, teeth 96 slide with the grain, i.e., the teeth 96 are not oriented to catch the pawl 90 and, likewise, the pawl 90 is not oriented to catch the teeth 96. However, in each of the rotation directions, the pawl 90 and gear teeth 96 have a sufficiently close relationship such that the user turning the disk 44 can feel each of the gear teeth 96 as each of the gear teeth 96 hits the pawl 90. As each of the gear teeth 96 is processed by the pawl 90, the user can feel the change in tightness of the seals 24, 26 and their flared portions 40, 42 against the face about the eyes.

When the pawl 90 is resiliently retracted radially or inwardly, the pawl 90 does not catch the teeth 96.

When the pawl 90 is rotated with the grain, i.e., in the direction where the pawl 90 and teeth 96 are not opposing each other, the pawl 90 does not catch the teeth 96.

The pawl 90 catches teeth 96 when the pawl 90 is not resiliently retracted and when the pawl 90 and teeth 96 are opposed to each other. This situation occurs when the rack 46 is moved (instead of the disk 44 being moved) so as to increase the distance of the headband 16 or 16A.

Rack 46 includes teeth 106 aligned in a straight line. Rack teeth 106 engage pinion teeth 108. When pinion teeth 108 are driven to rotate in either rotation direction by rack teeth 106, this action does not squeeze the pawl base 88. Nor does this action resiliently retract the pawl 90.

When the rack 46 is moved by hand (not by disk 44) to decrease the effective length of the headband 16 or 16A, the pinion teeth 108 are driven by the rack teeth 106 so as to rotate the pawl 90 with the grain of the gear teeth 96 such that there is no catching between the pawl 90 and gear teeth 96.

When the rack 46 is moved by hand (not by disk 44) to increase the effective length of the headband 16 or 16A, the pinion teeth 108 are driven by the rack teeth 106 so as to rotate the pawl 90 against the grain of the gear teeth 96 such that the pawl 90 immediately catches one of the gear teeth 96, whereupon the extension 100 to which the pawl 90 is engaged moves radially outwardly, thereby increasing the power of the bite between the pawl 90 and the tooth 96 to which the pawl 90 is caught.

Figure 5B:
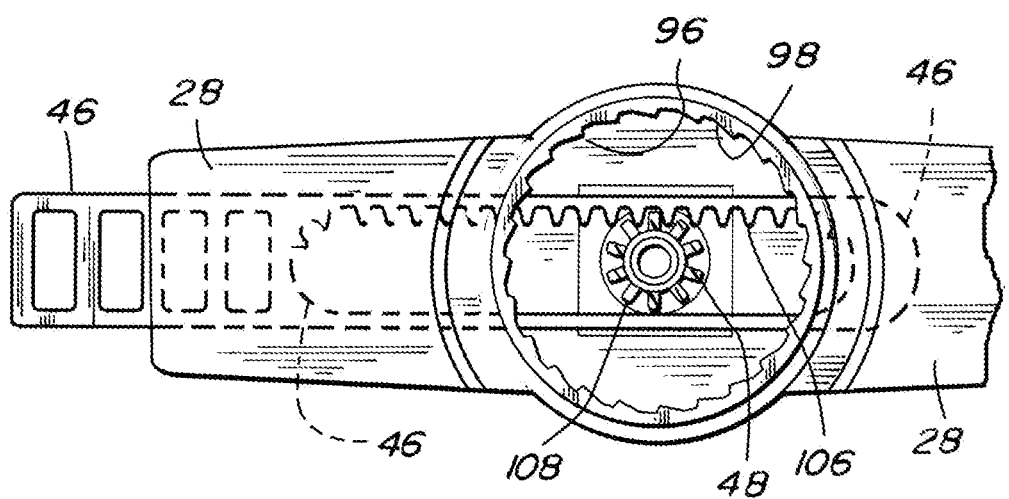
FIG. 5B is a view at lines 5B-5B of FIG. 5A.

FIG. 5B shows the rack channel 110 that runs from one end of the base or temple portion 28, through the base or temple portion 28 and adjacent to the fixed gear 98, and to the other end of the base or temple portion 28 such that rack channel 110 is open at two ends. One open end is the slot 50 shown in FIG. 1A where one end of the rack 46 exits the rack channel 110.

Base or temple portion 28 includes a pair of arcuate depressions 112 formed therein about the fixed gear 98 so as to ensure that the circumferential portion of the disk 44 is free to rotate relative to the outer side of the base or temple portion 28.

Rack 46 includes an elongate opening or elongate slot 114. Rack teeth 106 are formed on an upper edge of this slot 114. Rack 46 further includes a set of rectangular openings 116 on one end of the rack 46 so as to reduce the weight or mass of the rack 46.

FIG. 5B shows the pinion teeth 108 meshing with the rack teeth 106. FIG. 5B shows the rack 46 in the rack channel 110 of the temple portion 28.

Figure 6A:
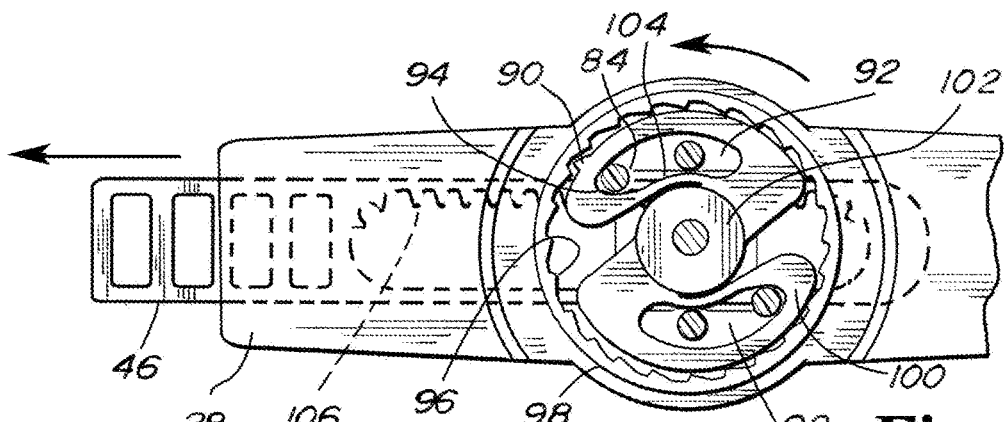
FIG. 6A is a view at lines 6A-6A of FIG. 5A with the rotatable adjustment apparatus being turned counter-clockwise to increase the effective length of the headband.

FIG. 6A shows that rotation of disk 44 in a first direction increases the effective length of the headband 16 or 16A. Disk 44 rotates pins 84, which engage the pawl base 88, which turn the pinion teeth 108, which drives the rack teeth 106, which slide the rack 46 in a straight direction out of the temple portion 28, which increases the effective length of the headband 16 or 16A and thereby loosens the seals 24, 26 and their flared portions 40, 42 about the eyes.

Figure 6B:
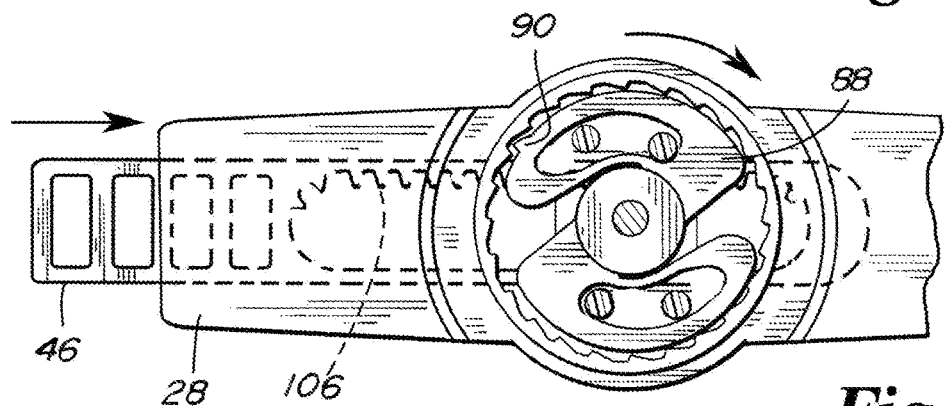
FIG. 6B is a view of FIG. 6A with the rotatable adjustment apparatus being turned clockwise to decrease the effective length of the headband.

FIG. 6B shows that rotation of disk 44 in a second direction decreases the effective length of the headband 16 or 16A. Disk 44 rotates pins 84, which engage the pawl base 88, which turn the pinion teeth 108, which drives the rack teeth 106, which slide the rack 46 in a straight direction into the temple portion 28 and out of slot 50 (shown in FIG. 1A), which decreases the effective length of the headband 16 or 16A and thereby tightens the seals 24, 26 and their flared portions 40, 42 about the eyes.

In the embodiment of FIGS. 6A and 6B, the rack 46 is disposed such that the rack teeth 106 are disposed along an upper edge of slot 114 and along an upper internal edge of rack channel 110.

Figure 6C:
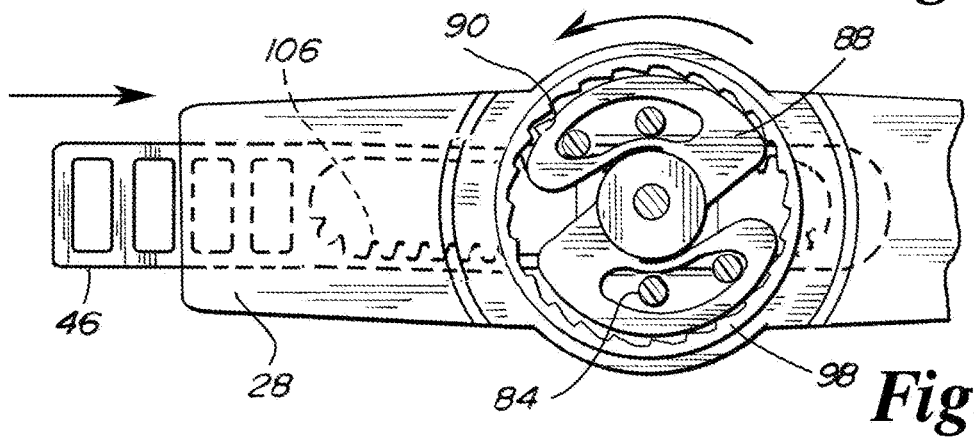
FIG. 6C is a view of the rotatable adjustment apparatus of FIG. 5A with the rack having teeth on the edge opposite of that shown in FIG. 6A and with the rotatable adjustment apparatus being turned counter-clockwise to decrease the effective length of the headband.

FIG. 6C shows that rotation of disk 44 in a first direction decreases the effective length of the headband 16 or 16A. Disk 44 rotates pins 84, which engage the pawl base 88, which turn the pinion teeth 108, which drives the rack teeth 106, which slide the rack 46 in a straight direction into the temple portion 28 and out of the slot 50 (shown in FIG. 1A), which decreases the effective length of the headband 16 or 16A and thereby tightens the seals 24, 26 and their flared portions 40, 42 about the eyes.

Figure 6D:
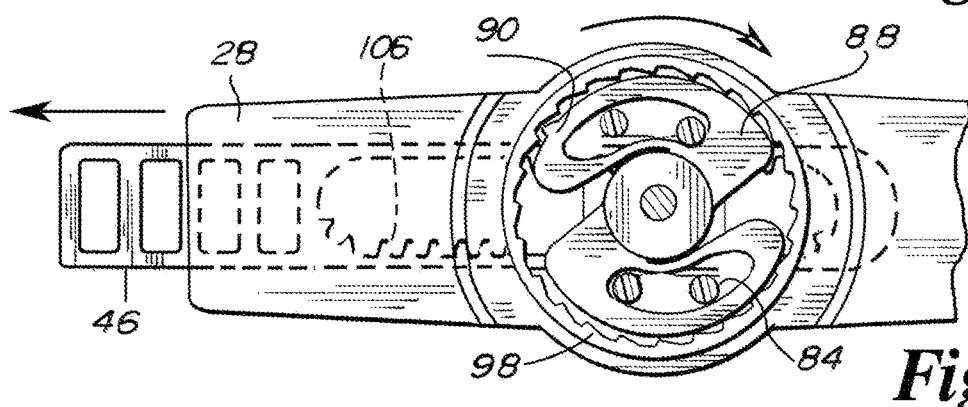
FIG. 6D is a view of the rotatable adjustment apparatus of FIG. 6C with the rotatable adjustment apparatus being turned clockwise to increase the effective length of the headband.

FIG. 6D shows that rotation of disk 44 in a second direction increases the effective length of the headband 16 or 16A. Disk 44 rotates pins 84, which engage the pawl base 88, which turn the pinion teeth 108, which drives the rack teeth 106, which slide the rack 46 in a straight direction out of the temple portion 28, which increases the effective length of the headband 16 or 16A and thereby loosens the seals 24, 26 and their flared portions 40, 42 about the eyes.

In the embodiment of FIGS. 6C and 6D, the rack 46 is disposed such that the rack teeth 106 are disposed along a lower edge of slot 114 and along a lower internal edge of rack channel 110.

Figure 7:
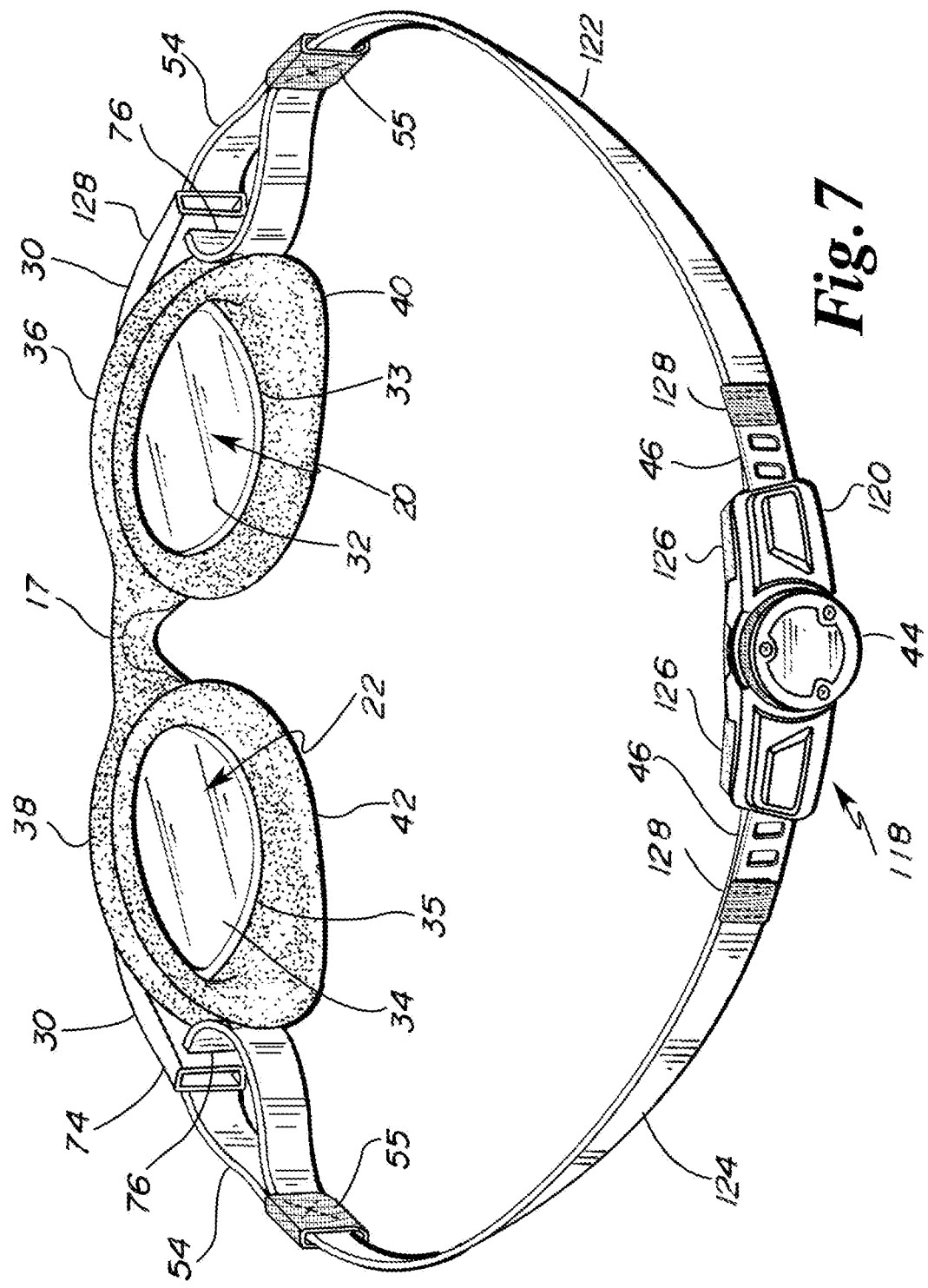
FIG. 7 shows a front perspective view of a ninth embodiment of the present invention where a pair of eye pieces has a rotatable adjustment apparatus at a rear portion of the headband and non-adjustable mechanisms adjacent to each of the eye pieces.

The FIG. 7 embodiment of the present pair of eye pieces includes a rotatable adjustment apparatus 118 with a base 120, first and second racks 46, a resilient and flexible headband portion 122 engaged to one of the racks 46, and a resilient and flexible headband portion 124 engaged to the other of the racks 46. Engaged to the rear of the base 120 is an arcuate resilient cushion 126 that is disposed between the base 120 and the back of the head. Adhesive or stitching 128 engages the outer ends of the racks 46 to the headband portions 122, 124.

In the FIG. 7 embodiment, the left eye superstructure is the superstructure 74 of FIGS. 3C and 4C.

In the FIG. 7 embodiment, the right eye superstructure 128 is identical to left eye superstructure 74 except that this right eye superstructure 128 is a mirror image of the left eye superstructure 74. In other words, each of superstructure 74, 128 includes an oblique tubular portion 30 having front and rear slots 76 for passage therethrough of the looped headband end portion 54. If desired, oblique portion 30 may be formed of a solid lightweight plastic instead of being tubular, which tubular feature provided for the reception of portions of the rotatable adjustment apparatus 18 such as rack 46. Here, without the rotatable adjustment apparatus 18, oblique portion 30 may be solid from front to back, from top to bottom, and from end to end, with the exception of through slot 76.

Superstructures 74, 128 further include plates 32, 34 and endless sidewalls or circumferential lips 33, 35.

The embodiment of FIG. 7 further includes the bridge 17, base portions 36, 38, and flared portions 40, 42 to provide a suction cup function to this FIG. 7 embodiment. All embodiments of the present pair of eye pieces have this suction cup function.

Like the eye piece pair embodiment shown in FIG. 3C, the glued or stitched looped headband end portion 54 is permanent and intended to be a permanent nonadjustable connection to the left eye superstructure 74. "Permanent" means that the nonadjustable connection is disconnectable from the left eye superstructure 74 only if the integrity of the non-adjustable connection is destroyed such as by cutting or tearing or breaking of the headband end portion 54 or oblique portion 30 to which the looped headband end portion 54 is connected.

Figure 8:
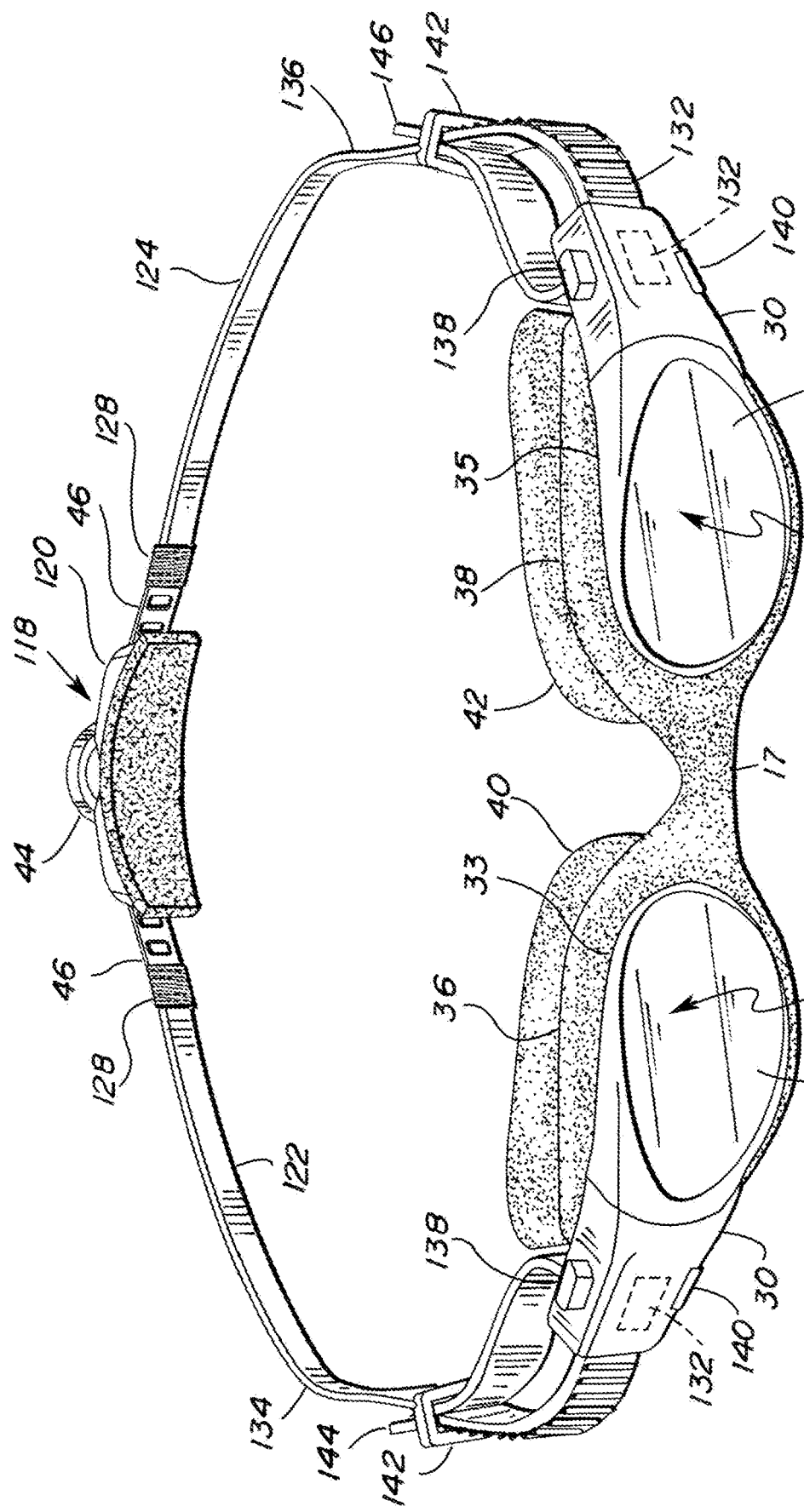
FIG. 8 shows a front perspective view of a tenth embodiment of the present invention where a pair of eye pieces has a rotatable adjustment apparatus at a rear portion of the headband and adjustable mechanisms adjacent to each of the eye pieces.
Figure 9A:
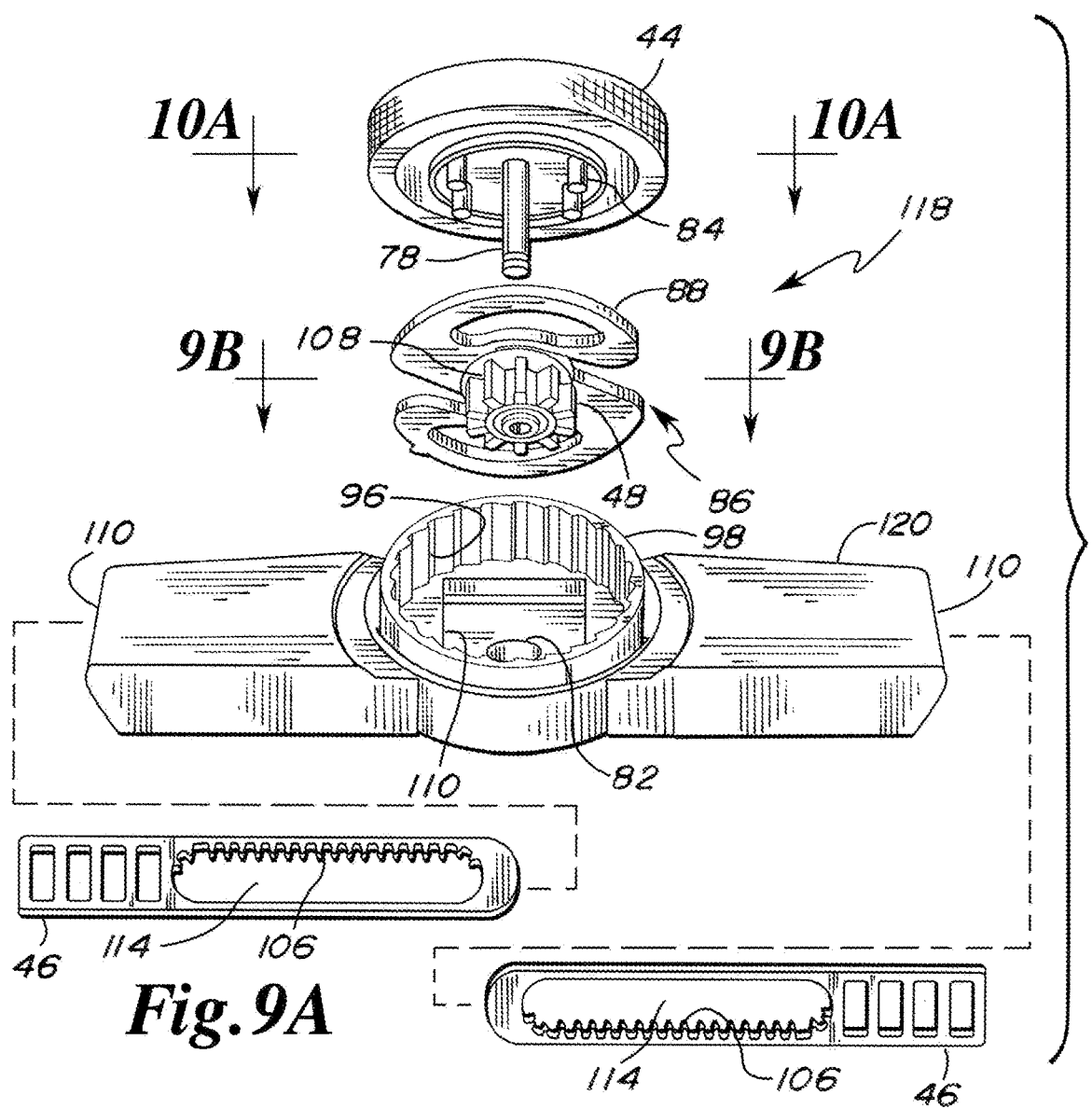
FIG. 9A is an exploded perspective view of the rotatable adjustment apparatus for any of the rotatable adjustors of FIGS. 7 and 8.
Figure 9B:
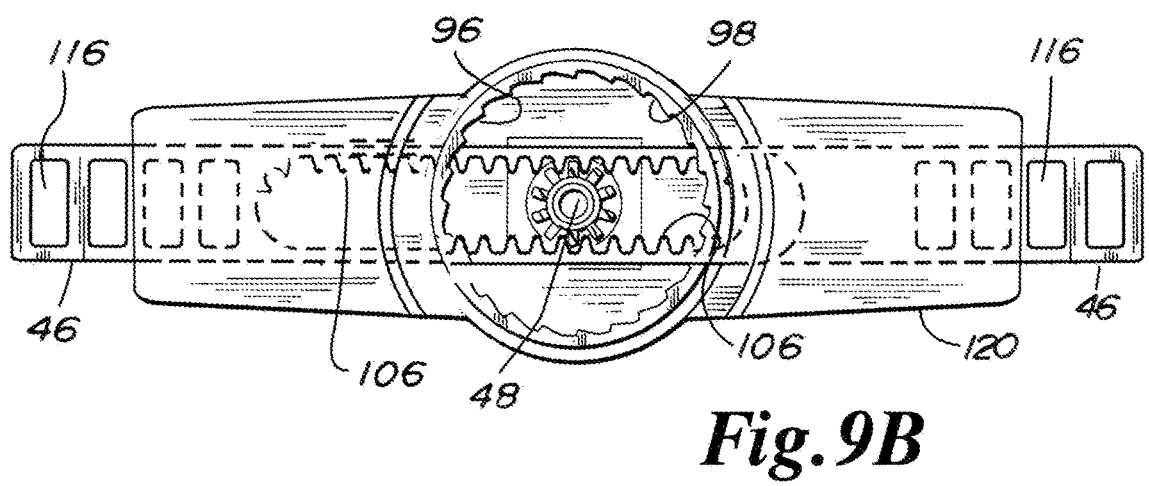
FIG. 9B is a view at lines 9B-9B of FIG. 9A.

The eye piece pair embodiment of FIG. 8 is identical to the embodiment of FIG. 7 except that there is a nonrotatable adjustment mechanism between the headband portions 122, 124 and the oblique portions 30. Each of the oblique portions 30 houses a pivotable biased pawl 130 that engages ribs or ribbing 132 formed on the sides of distal ends 134, 136 of the headband portions 122, 124. Pawl 130 is biased to the engaged position such that it takes more force to increase the effective length of the headband portions 122, 124 than it takes to decrease the effective length of the headband portions 122, 124. When push buttons 138, 140 are squeezed, such pivots the pawl 132 away from the ribbing 132 such that the ribbing 132 may be easily with minimal resistance pulled through the slotted end of the oblique portions 30. When push buttons 138, 140 are released, the pawl 132 pivots back to an engaged position with ribbing 132. Push buttons 138, 140 are biased outwardly to a position where the push buttons 138, 140 permit the pawl 132 to engage ribbing 132. A rectangular plastic piece 142 captures the free portions 144, 146 of the distal ends 134, 136 to minimize stray end portions of the headband. Piece 142 encircles free portions 144, 146 and sections of the distal ends 134, 136.

Rotatable adjustment apparatus 118 is shown in FIGS. 9A, 9B, 10A, and 10B. Rotatable adjustment apparatus 118 is identical to rotatable adjustment apparatus 18 except that first and second racks 46 are employed, where the racks 46 are identical except that one rack 46 is inserted into tubular base 120 where rack teeth 106 are disposed along an upper edge that partially forms slot 114 and except that the other rack 46 is inserted into tubular base 120 where rack teeth 106 are disposed along a lower edge that partially forms slot 114. Pinion teeth 108 have sufficient depth to drive both racks 46 at the same time.

FIG. 10A shows that when the disk 44 is rotated counter-clockwise (when the top portion of the disk 44 is rotated to the left), then the racks 46 slide outwardly so as to increase the effective length of the headband, i.e., headband portions 122, 124, so as to loosen the suction cup fit about the eyes.

FIG. 10B shows that when the disk 44 is rotated clockwise (when the top portion of the disk 44 is rotated to the right), then the racks 46 slide inwardly so as to decrease the effective length of the headband, i.e., headband portions 122, 124, so as to tighten the suction cup fit about the eyes.

It should be noted that in certain embodiments there are two rotatable adjustment apparatus 18 on one pair of eye pieces. These are the embodiments shown in FIGS. 1A, 1B, 2A, 2B, 3A, 3B, 4A, and 4B. In other words, one rotatable adjustment apparatus 18 is on the right eye superstructure and the other rotatable adjustment apparatus is on the left eye superstructure. Depending upon which rack 46 is used, i.e., where the rack 46 has upper teeth 106 or lower teeth 106, there are the following possible combinations of 1) A-B and A-B, 2) A-B and C-D, 3)C-D and A-B, and 4)C-D and C-D:

First Combination

A-B. The first rotatable adjustment apparatus being engaged to the right eye superstructure and is turnable clockwise and counter-clockwise, the effective length of the headband being decreased when the first rotatable adjustment apparatus is turned clockwise, the effective length of the headband being increased when the first rotatable adjustment apparatus is turned counter-clockwise, with clockwise and counter-clockwise being determined by a viewer looking at the right side of the head of a person wearing the protective eye piece apparatus; and A-B. The second rotatable adjustment apparatus being engaged to the left eye superstructure and being turnable clockwise and counter-clockwise, the effective length of the headband being decreased when the second rotatable adjustment apparatus is turned clockwise, the effective length of the headband being increased when the second rotatable adjustment apparatus is turned counter-clockwise, with clockwise and counter-clockwise being determined by a viewer looking at the left side of the head of a person wearing the protective eye piece apparatus.

Second Combination

A-B. The first rotatable adjustment apparatus being engaged to the right eye superstructure and is turnable clockwise and counter-clockwise, the effective length of the headband being decreased when the first rotatable adjustment apparatus is turned clockwise, the effective length of the headband being increased when the first rotatable adjustment apparatus is turned counter-clockwise, with clockwise and counter-clockwise being determined by a viewer looking at the right side of the head of a person wearing the protective eye piece apparatus; and C-D. The second rotatable adjustment apparatus being engaged to the left eye superstructure and being turnable clockwise and counter-clockwise, the effective length of the headband being increased when the second rotatable adjustment apparatus is turned clockwise, the effective length of the headband being decreased when the second rotatable adjustment apparatus is turned counter-clockwise, with clockwise and counter-clockwise being determined by a viewer looking at the left side of the head of a person wearing the protective eye piece apparatus.

Third Combination

C-D. The first rotatable adjustment apparatus is engaged to the right eye superstructure and is turnable clockwise and counter-clockwise, the effective length of the headband being increased when the first rotatable adjustment apparatus is turned clockwise, the effective length of the headband being decreased when the first rotatable adjustment apparatus is turned counter-clockwise, with clockwise and counter-clockwise being determined by a viewer looking at the right side of the head of a person wearing the protective eye piece apparatus; and A-B. The second rotatable adjustment apparatus being engaged to the left eye superstructure and being turnable clockwise and counter-clockwise, the effective length of the headband being decreased when the second rotatable adjustment apparatus is turned clockwise, the effective length of the headband being increased when the second rotatable adjustment apparatus is turned counter-clockwise, with clockwise and counter-clockwise being determined by a viewer looking at the left side of the head of a person wearing the protective eye piece apparatus.

Fourth Combination

C-D. The first rotatable adjustment apparatus being engaged to the right eye superstructure and is turnable clockwise and counter-clockwise, the effective length of the headband being increased when the first rotatable adjustment apparatus is turned clockwise, the effective length of the headband being decreased when the first rotatable adjustment apparatus is turned counter-clockwise, with clockwise and counter-clockwise being determined by a viewer looking at the right side of the head of a person wearing the protective eye piece apparatus; and C-D. The second rotatable adjustment apparatus being engaged to the left eye superstructure and being turnable clockwise and counter-clockwise, the effective length of the headband being increased when the second rotatable adjustment apparatus is turned clockwise, the effective length of the headband being decreased when the second rotatable adjustment apparatus is turned counter-clockwise with clockwise and counter-clockwise being determined by a viewer looking at the left side of the head of a person wearing the protective eye piece apparatus.

It should be noted that that the size of a human head surprisingly varies little. Thus the embodiments without the nonrotatable adjustment mechanisms 60 of FIGS. 2A, 2B, 2C, 4A, 4B, 4C are preferred. Likewise the embodiments without the buttons 138, 140, pawl 132 and ribbing 132 of FIG. 8 are preferred. In other words, the embodiments of FIGS. 1A, 1B, 1C, 3A, 3B, 3C, and 7 are preferred over the embodiments of FIGS. 2A, 2B, 2C, 4A, 4B, 4C and 8. In still other words, the embodiments of FIGS. 1A, 1B, 1C, 3A, 3B, 3C, and 7 provide sufficient tightening and loosening by utilizing the rotatable adjustment apparatus 18 and 118 themselves with no aid from any other mechanism that may increase or decrease the length of the headband 16. Even if the human head varies significantly in diameter, the resiliency of the headband 16 and the length of the rack 46 provides more than sufficient range for most head sizes with no aid from any mechanism other than the rotatable adjustment apparatus 18 and 118.

It should also be noted that each tooth of the rack teeth 106 and pinion teeth 108 may be of a relatively small size or of a relatively minute size. Thus, since the rotatable adjustment apparatus 18 and 118 provides a different diameter or different tightness at each and every tooth 106, 108, and since the rotatable adjustment apparatus 18 or 118 locks at each and every tooth, a custom fit is easily and quickly obtainable.

It should be noted that headband 16, depending upon its width, length, thickness, and material or composition, may or may not slip readily about the head. When the headband 16 does not slip easily about the head, having two rotatable adjustment apparatus 18 on or integral with the superstructure of the right eye piece and on or integral with the superstructure of the left eye piece, such as shown in FIGS. 1A, 1B, 2A, 2B, 3A, 3B, 4A, and 4B, is preferred.

It should be noted that the base of the rotatable adjustment apparatus 18 is the superstructure temple portion 28 in FIGS. 1A, 1B, 1C, 2A, 2B, 2C. It should be noted that the base of the rotatable adjustment apparatus 18 is the superstructure oblique portion 30 in FIGS. 3A, 3B, 3C, 4A, 4B, and 4C. If desired, the base of the rotatable adjustment mechanism 18 may be engaged, such as by gluing or with pins, to the outside of one or more of the eye piece superstructures such that the rack 46 is outside of the eye piece superstructures.

The following U.S. patents are hereby incorporated by reference herein in their entireties: 1) the Hsing-Chi U.S. Pat. No. 5,357,654 A issued Oct. 25, 1994 and entitled Ratchet Diving Mask Strap, 2) the Chen U.S. Pat. No. 8,434,200 B2 issued May 7, 2013 and entitled Adjusting Device For Tightening Or Loosing Laces And Straps, and 3) the Pontano et al. U.S. Pat. No. 10,156,347 B2 issued Dec. 18, 2018 and entitled HeadGear Assembly And Components.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

What is claimed is:

1. A protective eye piece apparatus comprising:
   a) a right eye superstructure, the right eye superstructure comprising a right eye piece, the right eye piece being transparent to permit the right eye to see through the right eye piece, the right eye piece having a right eye piece circumference extending 360 degrees about the right eye piece;
   b) a left eye superstructure, the left eye superstructure comprising a left eye piece, the left eye piece being transparent to permit the left eye to see through the left eye piece, the left eye piece having a left eye piece circumference extending 360 degrees about the left eye piece;
   c) a right eye resilient seal extending rearwardly from the right eye piece circumference such that the right eye resilient seal extends 360 degrees about the right eye piece, the right eye resilient seal extending 360 degrees about the right eye of a user;
   d) a left eye resilient seal extending rearwardly from the left eye piece circumference such that the left eye resilient seal extends 360 degrees about the left eye piece, the left eye resilient seal extending 360 degrees about the left eye of the user;
   e) the right eye piece being spaced from the left eye piece;
   f) the right eye resilient seal being spaced from the left eye resilient seal;
   g) a resilient bridge extending between the right eye superstructure and the left eye superstructure;
   h) a resilient headband engaged between the right and left superstructures, the resilient headband adapted to extend about a head of the user;
   i) a first rotatable adjustment apparatus engaged to the resilient headband and adapted to increase and decrease an effective length of the headband to tighten and loosen the right and left eye resilient seals about the right and left eyes of the user; and
   j) wherein the first rotatable adjustment apparatus comprises:
      i) a base having a toothed gear;
      ii) a rack and pinion apparatus having a rack and pinion;
      iii) a pawl apparatus having a pawl that engages the toothed gear;
      iv) the pawl being resiliently engaged between the toothed gear and the pinion;
      v) the pinion being lockable by an engagement between the pawl and toothed gear such that the rack may be slid in only one of first and second directions; and
      vi) the pinion being unlockable by a disengagement between the pawl and toothed gear such that the rack may be slid in each of the first and second directions.

2. The protective eye piece apparatus of claim 1, wherein the first rotatable adjustment apparatus is engaged to the right eye superstructure.

3. The protective eye piece apparatus of claim 2, and further comprising a second rotatable adjustment apparatus being engaged to the left eye superstructure.

4. The protective eye piece apparatus of claim 1, wherein the first rotatable adjustment apparatus is engaged to the left eye superstructure.

5. The protective eye piece apparatus of claim 1, wherein the first rotatable adjustment apparatus is intermediate of the right and left eye superstructure and is engaged to the resilient headband such that a first portion of the resilient headband extends from the first rotatable adjustment apparatus to the right eye superstructure and such that a second portion of the resilient headband extends from the first rotatable adjustment apparatus to the left eye superstructure.

6. The protective eye piece apparatus of claim 1, wherein the base includes a slot formed therein, the rack engaged to the resilient headband and adapted to slide in the first and second directions in the slot formed in the base.

7. The protective eye piece apparatus of claim 6, wherein the base of the first rotatable adjustment apparatus is integral with one of the right and left eye superstructures.

8. The protective eye piece apparatus of claim 1, wherein the base of the first rotatable adjustment apparatus is integral with one of the right eye and left eye superstructures.

9. The protective eye piece apparatus of claim 1, wherein the first rotatable adjustment apparatus is engaged to the right eye superstructure and is turnable clockwise and counter-clockwise, the effective length of the headband being decreased when the first rotatable adjustment apparatus is turned clockwise, the effective length of the headband being increased when the first rotatable adjustment apparatus is turned counter-clockwise, with clockwise and counter-clockwise being determined by a viewer looking at the right side of the head of a person wearing the protective eye piece apparatus.

10. The protective eye piece apparatus of claim 9, and further comprising a second rotatable adjustment apparatus being engaged to the left eye superstructure and being turnable clockwise and counter-clockwise, the effective length of the headband being decreased when the second rotatable adjustment apparatus is turned clockwise, the effective length of the headband being increased when the second rotatable adjustment apparatus is turned counter-clockwise, with clockwise and counter-clockwise being determined by a viewer looking at the left side of the head of a person wearing the protective eye piece apparatus.

11. The protective eye piece apparatus of claim 9, and further comprising a second rotatable adjustment apparatus being engaged to the left eye superstructure and being turnable clockwise and counter-clockwise, the effective length of the headband being increased when the second rotatable adjustment apparatus is turned clockwise, the effective length of the headband being decreased when the second rotatable adjustment apparatus is turned counter-clockwise, with clockwise and counter-clockwise being determined by a viewer looking at the left side of the head of a person wearing the protective eye piece apparatus.

12. The protective eye piece apparatus of claim 1, wherein the first rotatable adjustment apparatus is engaged to the right eye superstructure and is turnable clockwise and counter-clockwise, the effective length of the headband being increased when the first rotatable adjustment apparatus is turned clockwise, the effective length of the headband being decreased when the first rotatable adjustment apparatus is turned counter-clockwise, with clockwise and counter-clockwise being determined by a viewer looking at the right side of the head of a person wearing the protective eye piece apparatus.

13. The protective eye piece apparatus of claim 12, and further comprising a second rotatable adjustment apparatus being engaged to the left eye superstructure and being turnable clockwise and counter-clockwise, the effective length of the headband being decreased when the second rotatable adjustment apparatus is turned clockwise, the effective length of the headband being increased when the second rotatable adjustment apparatus is turned counter-clockwise, with clockwise and counter-clockwise being determined by a viewer looking at the left side of the head of a person wearing the protective eye piece apparatus.

14. The protective eye piece apparatus of claim 12, and further comprising a second rotatable adjustment apparatus engaged to the left eye superstructure and being turnable clockwise and counter-clockwise, the effective length of the headband being increased when the second rotatable adjustment apparatus is turned clockwise, the effective length of the headband being decreased when the second rotatable adjustment apparatus is turned counter-clockwise with clockwise and counter-clockwise being determined by a viewer looking at the left side of the head of a person wearing the protective eye piece apparatus.

15. A protective eye piece apparatus comprising:
   a) a right eye superstructure, the right eye superstructure comprising a right eye piece, the right eye piece being transparent to permit the right eye to see through the right eye piece, the right eye piece having a right eye piece circumference extending 360 degrees about the right eye piece;
   b) a left eye superstructure, the left eye superstructure comprising a left eye piece, the left eye piece being transparent to permit the left eye to see through the left eye piece, the left eye piece having a left eye piece circumference extending 360 degrees about the left eye piece;
   c) a right eye resilient seal extending rearwardly from the right eye piece circumference such that the right eye resilient seal extends 360 degrees about the right eye piece, the right eye resilient seal extending 360 degrees about the right eye of a user;
   d) a left eye resilient seal extending rearwardly from the left eye piece circumference such that the left eye resilient seal extends 360 degrees about the left eye piece, the left eye resilient seal extending 360 degrees about the left eye of the user;
   e) the right eye piece being spaced from the left eye piece;
   f) the right eye resilient seal being spaced from the left eye resilient seal;
   g) a resilient bridge extending between the right eye superstructure and the left eye superstructure;
   h) a resilient headband engaged between the right and left superstructures, the resilient headband adapted to extend about a head of the user;
   i) a first rotatable adjustment apparatus engaged to the resilient headband and adapted to increase and decrease an effective length of the headband to tighten and loosen the right and left eye resilient seals about the right and left eyes of the user; and
   j) wherein the first rotatable adjustment apparatus comprises a base and a ratchet apparatus, the base having an annulus with a toothed inner face, the ratchet apparatus comprising gearing having a pawl, the pawl engaging the toothed inner face of the annulus, the gearing engaging the resilient headband, the pawl being adapted to permit at all times said effective length of the headband to be decreased.

16. The protective eye piece apparatus of claim 15, wherein the base of the first rotatable adjustment apparatus is integral with one of the right and left eye superstructures.

\* \* \* \* \*